United States Patent
Lock et al.

(10) Patent No.: US 12,414,739 B2
(45) Date of Patent: Sep. 16, 2025

(54) SYSTEM AND METHOD FOR SWITCHING THE DESIGNATION OF A BIOSIGNAL SENSOR

(71) Applicant: COAPT LLC, Chicago, IL (US)

(72) Inventors: Blair Andrew Lock, Chicago, IL (US); Levi John Hargrove, Chicago, IL (US); Katherine Cai, Chicago, IL (US); Gila Baer, Chicago, IL (US); Mary McMeekin, Chicago, IL (US); Kevin Dwyer, Chicago, IL (US); Steven Hansen, Chicago, IL (US)

(73) Assignee: COAPT LLC, Chicago, IL (US)

( * ) Notice: Subject to any disclaimer, the term of this patent is extended or adjusted under 35 U.S.C. 154(b) by 625 days.

(21) Appl. No.: 17/533,573

(22) Filed: Nov. 23, 2021

(65) Prior Publication Data

US 2023/0157636 A1    May 25, 2023

(51) Int. Cl.
| | |
|---|---|
| A61B 5/00 | (2006.01) |
| A61B 5/28 | (2021.01) |
| A61B 5/291 | (2021.01) |
| A61B 5/296 | (2021.01) |
| A61B 5/297 | (2021.01) |

(52) U.S. Cl.
CPC .............. *A61B 5/681* (2013.01); *A61B 5/28* (2021.01); *A61B 5/291* (2021.01); *A61B 5/296* (2021.01); *A61B 5/297* (2021.01); *A61B 5/4836* (2013.01); *A61B 2562/0219* (2013.01); *A61B 2562/0247* (2013.01); *A61B 2562/0271* (2013.01)

(58) Field of Classification Search
CPC ........... A61B 5/681; A61B 5/28; A61B 5/291; A61B 5/296; A61B 5/297; A61B 5/4836; A61B 2562/0219; A61B 2562/0247; A61B 2562/0271; A61B 5/318; A61B 5/304
See application file for complete search history.

(56) References Cited

U.S. PATENT DOCUMENTS

| | | | |
|---|---|---|---|
| 10,582,868 B1 * | 3/2020 | Ahmad | A61B 5/339 |
| 2017/0011210 A1 * | 1/2017 | Cheong | A61B 5/681 |
| 2020/0367776 A1 * | 11/2020 | Matsumoto | H03F 3/387 |

* cited by examiner

*Primary Examiner* — Paula J Stice
(74) *Attorney, Agent, or Firm* — MARSHALL, GERSTEIN & BORUN LLP

(57) ABSTRACT

Adaptive biosignal systems and methods are disclosed for switching one or more designations of biosignal sensors for dynamic adaptation and optimization of one or more biosignal detection devices. A sensor designation cycle is executed for a plurality of biosignal sensors of a biosignal detection device, each of the plurality of biosignal sensors configured to collect biosignal data of a user, and each of the plurality of biosignal sensors having a designation defining an electrical sensor modality modifiable by a switch communicatively coupled to the biosignal detection device. The plurality of biosignal sensors comprises at least a first biosignal sensor, a second biosignal sensor, and a third biosignal sensor, wherein the first biosignal sensor is designated as a reference sensor, and wherein the second biosignal sensor is designated as a measurement sensor. The sensor designation cycle comprises various algorithms for switching designations of the various sensors.

21 Claims, 7 Drawing Sheets

SYSTEM AND METHOD FOR SWITCHING THE DESIGNATION OF A BIOSIGNAL SENSOR

FIELD OF THE DISCLOSURE

The present disclosure generally relates to adaptive biosignal systems and methods and electrode modality, and more particularly, to adaptive biosignal systems and methods configured to switch one or more designations of biosignal sensors for dynamic adaptation and optimization of one or more biosignal detection devices.

BACKGROUND

Conventional medical and consumer technologies can collect biosignal information from a user. However, as the need for such technology grows, the importance of having cost-effective hardware that can improve product functionality becomes increasingly important. In many scenarios, current technologies are measuring biosignals of users with fewer hardware components; maximizing product functionality while minimizing the cost of the physical aspects of the product. For example, ultrasound transducers, optical sensors, and processors are all being optimized to fit into smaller spaces while maintaining their ability to collect the same, or more, biosignal information. This is exemplified by products like the APPLE WATCH device; using traditional dry electrodes to take an electrocardiogram measurement. In many similar electrode utilizing devices, pairs of electrodes collect electrical signals generated from user tissues to determine biological properties, such as muscle movement, nervous system activity, or even deliver a stimulus to drive a muscle contraction.

However, these systems typically control electrode functionality with a pair of measurement electrodes with a tertiary ground electrode for the purpose of common mode subtraction. In these devices, three electrodes are required to generate a single electrode-pair biosignal measurement data stream, each having two measurement sensors (for measuring electrical potential difference), and one ground electrode. Further, in these devices, additional data streams can be added through the addition of an additional electrode pair. For each pair of electrodes added, the devices are then able to collect a new stream of biosignal data from the user. For example, a system maintaining a three-electrode biosignal detection device may have designated two of the three electrodes as measurement sensors and the third as a designated ground electrode; creating a single stream of measurement data for analysis. Should the manufacturer desire to increase the number of incoming data streams from one to two data streams, they would traditionally need to increase the number of electrodes on the device from three to five, adding two more electrodes to create a biosignal detection device with two pairs of measurement electrodes (four measurement electrodes total) all being referenced against the single ground electrode (totaling five electrodes). This can become costly as adding new data streams requires a minimum of a two-electrode addition to the technology in addition to space requirements, power, and connecting equipment, all required to facilitate the newly added electrodes. This is in addition to creating new fabrication and/or manufacturing facilities, assembly lines, or the like to create the new devices, which may each differ based on user specific or task specific need.

For the foregoing reasons, there is a need for a system that has the capacity to increase the number of sampling biosignal sensor data streams without adding additional sensor equipment to optimize product cost, biosignal sensor sampling coverage, and increase product functionality.

BRIEF SUMMARY

For the aforementioned reasons, there is a need for a technology that allows a biosignal detection device to alter the designations for which biosignal sensors function, e.g., alter the modality of one or more biosignal sensors of a given biosignal detection device to allow for dynamic adaptation. More specifically, there is a need for an intelligent switch that optimizes the biosignal sensor designation process and to take advantage of the possible biosignal sensor permutations inherent within many current sensor-based technologies for an optimized biosignal detection experience. The inventions of the present disclosure overcome existing techniques that require multiple sensors, but do so in one-dimensional, fixed, rigid, and/or otherwise ineffective manner.

Accordingly, the present disclosure describes adaptive biosignal systems and methods for switching one or more designations of biosignal sensors for dynamic adaptation and optimization of one or more biosignal detection devices. This functionality is accomplished through a switch-enabled biosignal detection device, having the capacity to designate which of the available biosignal sensors will represent a measurement sensor, which will designate a reference (e.g. "ground") sensor, and which pairs of electrodes will be utilized for data collection. In various aspects, a biosignal detection device implementing this functionality is configured to adapt (e.g., increase, decrease, or modify) the number of available biosignal sensor measurement pairs through a switch and has the ability to collect and adapt biosignal data from many permutations of biosignal sensors, which may include with or without adding new biosignal sensors to the biosignal detection device. In various aspects, the adaptive biosignal systems and methods of the present disclosure overcome the issues of prior art biosignal devices by providing the capability to alter, adjust, or create additional data streams for their devices without the necessity of adding additional electrodes to the current subset of hardware.

For example, through the disclosed invention, a biosignal system has the new capability to collect biosignal data from many different permutations of biosignal sensors without, in some aspects, needing to add new hardware—both allowing increased coverage of biosignal detection devices and facilitating a reduction in device cost through hardware reduction. In several of the disclosed aspects, adaptive biosignal systems and methods are described with the capacity to alter the designation of coupled biosignal sensors. The adaptive biosignal systems and methods comprise at least three biosignal sensors configured to measure biosignals (i.e., biosignal data) from a user. The biosignal data may be detected when a user moves, contracts, or otherwise uses his or her muscles, thereby causing the generation of electrical or signal data from the user's body (e.g., such as at an arm, leg, or other portion of the body). The adaptive biosignal systems and methods may further a switch configured to change the designation of at least one of the biosignal sensors and a processor configured to execute a software component that instructs the switch how to perform the change in designation for each of the biosignal sensors. For example, in a three-biosignal sensor system, where each of the biosignal sensors is a surface electromyographic electrode, two of the three biosignal sensors may be configured as measurement electrodes, where the electrical potential between the measurement electrodes is measured as an electromyographic event. Each of these electrodes may then be shorted to a third sensor, e.g., a reference sensor (e.g., a ground electrode) for common mode subtraction thereby removing ambient noise artifacts from the collected dataset. The processor, then through executing the software component, enables the switch to alter the designation of the biosignal sensors for either a measurement sensor or a reference sensor, changing the designation from one to the other, respectively.

In the present example, the first of the two measurement sensors may have its designation changed to a reference sensor while the reference sensor has its designation changed to a measurement sensor. In this example, the location for both the reference sensor and the measurement sensor (through being re-designated) has spatially changed about the patient's body (e.g., arm) thereby providing a new physical location, and thus a new source, of biosignal data or otherwise information to be collected. The processor may then alter the designation for the final sensor that has not been designated as a reference sensor; causing the third permutation for the set of three sensors, and, thereby, the third unique source of biosignal data to be collected. This effectively allows the system to collect multiple different sources of signal data with the same biosignal sensors.

It is to be understood that the foregoing examples are non-limiting, such that the switch may can have any number of inputs and throws. That is, the switch can have any number of leads coming into the switch, and the switch can have any number of outputs, as long as it can send and receive data. In addition, various and/or different or additional numbers of biosignal sensors may be used for a given adaptive biosignal system or method.

More specifically, in various aspects herein, an adaptive biosignal system is disclosed. The adaptive biosignal system is configured to switch one or more designations of biosignal sensors for dynamic adaptation and optimization of one or more biosignal detection devices. In various aspects, the adaptive biosignal system includes a biosignal detection device comprising a plurality of biosignal sensors. Each of the plurality of biosignal sensors are configured to collect biosignal data of a user. The plurality of biosignal sensors may comprise at least a first biosignal sensor, a second biosignal sensor, and a third biosignal sensor. The adaptive biosignal system may further comprise a switch communicatively coupled to the biosignal detection device and configured to modify a designation of one or more of the plurality of biosignal sensors. Each respective designation may define an electrical sensor modality. For example, the first biosignal sensor may be designated as a reference sensor, and the second biosignal sensor may be designated as a measurement sensor. The adaptive biosignal system may further comprise a processor communicatively coupled to the biosignal detection device. In addition, the adaptive biosignal system may further comprise a software component comprising computing instructions stored on a memory communicatively coupled to the processor, wherein the computing instructions, when executed by the processor, cause the processor to execute a sensor designation cycle comprising of at least one of: (a) switching the designation of the first biosignal sensor previously designated as a reference sensor to a measurement sensor; (b) switching the designation of the second biosignal sensor previously designated as a measurement sensor to a reference sensor; (c) designating the third biosignal sensor as either a measurement sensor or a reference sensor; and/or, (d) wherein the third biosignal sensor is designated as a measurement sensor, wherein the second biosignal sensor and the third biosignal sensor comprise an initial biosignal sensor group, and wherein biosignal data of the user measured by the initial biosignal sensor group is analyzed as a first dataset group, and switching the designation of the first biosignal sensor to a measurement sensor, and pairing either the first biosignal sensor with the second biosignal sensor or the third biosignal sensor to create a new biosignal sensor group, and wherein different biosignal data of the user is measured by the new biosignal sensor group as a second dataset group, the second dataset group being different from the first dataset group.

In addition, in various aspects herein, an adaptive biosignal method for switching one or more designations of biosignal sensors for dynamic adaptation and optimization of one or more biosignal detection devices is disclosed. The adaptive biosignal method may comprise executing a sensor designation cycle for a plurality of biosignal sensors of a biosignal detection device, where each of the plurality of biosignal sensors is configured to collect biosignal data of a user. In addition, each of the plurality of biosignal sensors has a designation defining an electrical sensor modality modifiable by a switch communicatively coupled to the biosignal detection device. The plurality of biosignal sensors may comprise at least a first biosignal sensor, a second biosignal sensor, and a third biosignal sensor, where the first biosignal sensor is designated as a reference sensor, and where the second biosignal sensor is designated as a measurement sensor. The adaptive biosignal method may further comprise, as part of the sensor designation cycle, of at least one of: (a) switching the designation of the first biosignal sensor previously designated as a reference sensor to a measurement sensor; (b) switching the designation of the second biosignal sensor previously designated as a measurement sensor to a reference sensor; (c) designating the third biosignal sensor as either a measurement sensor or a reference sensor; and/or; (d) wherein the third biosignal sensor is designated as a measurement sensor, wherein the second biosignal sensor and the third biosignal sensor comprise an initial biosignal sensor group, and wherein biosignal data of the user measured by the initial biosignal sensor group is analyzed as a first dataset group, and switching the designation of the first biosignal sensor to a measurement sensor, and pairing either the first biosignal sensor with the second biosignal sensor or the third biosignal sensor to create a new biosignal sensor group, and wherein different biosignal data of the user is measured by the new biosignal sensor group as a second dataset group, the second dataset group being different from the first dataset group.

In still further aspects herein, a tangible, non-transitory computer-readable medium storing instructions for switching one or more designations of biosignal sensors for dynamic adaptation and optimization of one or more biosignal detection devices is disclosed. The instructions, when executed by one or more processors, cause the one or more processors to: execute a sensor designation cycle for a plurality of biosignal sensors of a biosignal detection device, where each of the plurality of biosignal sensors is configured to collect biosignal data of a user. Each of the plurality of biosignal sensors may have a designation defining an electrical sensor modality modifiable by a switch communicatively coupled to the biosignal detection device. The plurality of biosignal sensors may comprise at least a first biosignal sensor, a second biosignal sensor, and a third biosignal sensor. For example, the first biosignal sensor may be designated as a reference sensor, and the second biosignal sensor may be designated as a measurement sensor. The instructions, when executed by one or more processors, cause the one or more processors, as part of the sensor designation cycle, to perform at of at least one of: (a) switching the designation of the first biosignal sensor previously designated as a reference sensor to a measurement sensor; (b) switching the designation of the second biosignal sensor previously designated as a measurement sensor to a reference sensor; (c) designating the third biosignal sensor as either a measurement sensor or a reference sensor; and/or; (d) wherein the third biosignal sensor is designated as a measurement sensor, wherein the second biosignal sensor and the third biosignal sensor comprise an initial biosignal sensor group, and wherein biosignal data of the user measured by the initial biosignal sensor group is analyzed as a first dataset group, and switching the designation of the first biosignal sensor to a measurement sensor, and pairing either the first biosignal sensor with the second biosignal sensor or the third biosignal sensor to create a new biosignal sensor group, and wherein different biosignal data of the user is measured by the new biosignal sensor group as a second dataset group, the second dataset group being different from the first dataset group.

In addition, in various aspects herein, an adaptive biosignal method is described for switching biosignal sensor designations of biosignal sensors of a biosignal detection device to generate varying permutations of dataset groups comprising reference data and measurement sensor data as collected by the biosignal sensors across one or more sensor designation cycles. In such aspects, the adaptive biosignal method may comprise designating a first biosignal sensor of a plurality of biosignal sensors as a reference sensor. Each of the plurality of biosignal sensors may be adaptably configured by a designation defining an electrical sensor modality. The adaptive biosignal method may further comprise designating each of a second biosignal sensor and a third biosignal sensor of the plurality of biosignal sensors as measurement sensors. The second biosignal sensor and the third biosignal sensor may comprise or form an initial measurement biosignal sensor group. The adaptive biosignal method may further comprise generating a measurement dataset group of measurement biosignal data of a user as collected from the initial measurement biosignal sensor group. The adaptive biosignal method may further comprise referencing the measurement biosignal data against reference data provided by the first biosignal sensor. The adaptive biosignal method may further comprise adapting one or more the plurality of biosignal sensors by at least one of: (a) switching the designation of the first biosignal sensor previously designated as a reference sensor to a measurement sensor; (b) switching the designation of the second biosignal sensor previously designated as a measurement sensor to a reference sensor, and/or; (c) switching the designation of either the first biosignal sensor or second biosignal sensor causing the first biosignal sensor or second biosignal sensor to be grouped with a different measurement sensor of the plurality of biosignal sensors, wherein switching the designation of the first biosignal sensor or second biosignal sensor results in the plurality of biosignal sensors comprising at least two biosignal sensors designated as measurement sensors comprising a new measurement biosignal sensor group and at least one biosignal sensor designated as a reference sensor. The adaptive biosignal method may further comprise collecting updated biosignal data of the user from at least one of: (a) the new measurement biosignal sensor group, and/or: (b) a biosignal sensor group comprising at least one biosignal sensor having a switched designation. The adaptive biosignal method may further comprise generating an output signal by referencing the updated biosignal data against reference data provided by at least one reference sensor.

In addition, in various aspects herein, an adaptive biosignal system is configured to switch designations of biosignal sensors for dynamic adaptation and optimization of one or more biosignal detection devices. The adaptive biosignal system may comprise a biosignal detection device comprising a plurality of biosignal sensors. Each of the plurality of biosignal sensors may be configured to collect biosignal data of a user and initiate a therapeutic modality. The adaptive biosignal system may further comprise a switch communicatively coupled to the biosignal detection device and configured to modify a designation of one or more of the plurality of biosignal sensors where each respective designation defines an electrical sensor modality. The adaptive biosignal system may further comprise a processor communicatively coupled to the biosignal detection device. The adaptive biosignal system may further comprise a software component comprising computing instructions stored on a memory communicatively coupled to the processor, wherein the computing instructions, when executed by the processor, cause the processor to: designate one or more of the plurality of biosignal sensors as: (a) a measurement sensor; (b) a reference sensor, or; (c) a therapeutic sensor.

Advantages of switching the designation of the biosignal sensors includes the allowance the system to measure multiple different locations about the user. By measuring the electrical potential difference through each of the available permutations of sensors, a software component analyzing the biosignal data comprises an improved capability of identifying biological events that may be sought by a user. For example, in an electromyographic system, determining the presence of a muscle contraction or the electrical potential different between two muscles.

Advantages further include increasing the directional area in which a biosignal detection device may compare sensor measurements; providing analytics engines with larger datasets of data or otherwise information. This may allow analytics engines, for example, to utilize a single electrode to compare against multiple other electrodes that are spatially oriented in different locations to receive unique sets of biosignal data or otherwise information based on the selected electrode permutation, or to compare biosignal data between muscles. This same electrode may then be designated to be compared against each of the other available electrodes, allowing the adaptive biosignal system or method to compare the electric potential between each of the muscles of a user that correspond to one or more electrodes. In many of these aspects, the additional allowance of data input enables the associated analytics engines to more effectively identify biological processes.

In addition, many of the aspects as described herein benefit from the amount of device space that is saved through utilizing less hardware. Because the disclosed invention enables biosensor enabled wearable devices to calculate more sensor relationships with fewer hardware components, the disclosed invention inherently facilitates the miniaturization and cost reduction for many of these products.

In many of the aspects as described, the system further incorporates a band, cuff, or otherwise wearable device that demonstrates a multi-sensor array for the collection of biosignals from a user. In these aspects, the changing of the designation of associated biosignal sensors of the biosignal detection device are designed to allow the system to gather as many different permutations of biosignal data from the user as possible. It is within these many permutations of paired biosignal sensors that the system provides advantages as a whole. In some of these aspects, the wearable device is custom designed to fit the anatomy of a specific user and may be configured to adapt more appropriately to their available and/or specific body type and/or biosignals and/or biosignal data. The customized wearable devices become especially advantageous in aspects wherein the user is an amputee, or otherwise has an uncommon body shape or size.

In many of the aspects still, the system may utilize a multitude of switches; being of either an electrical, electronic, and/or mechanical nature. These switches, either jointly or separately, share the capacity to alter the designation of one or more of the biosignal sensors. Through switching the designation of one or more biosignal sensors, the biosignal data as collected and analyzed by the processor yield different potential biosignal data levels between the biosignal sensors. Through this biosignal data, as analyzed, the adaptive biosignal systems and methods are then provided the capacity to provide more-informed patient or user-specific biosignal data or otherwise information analytics, based on the increased amount and diversity of collected biosignal data or otherwise information.

In many of the preferred aspects as described herein, the system for switching the designation of one or more biosignal sensors may comprise cutaneous electrodes for the purposes of measuring the electrical potential of the skin. It is to be understood that the biosignal sensors may be cutaneous, subcutaneous, or within a proximity to the user wherein the biosignal sensors may still collect biosignal data from the user. Additionally, the functioning mechanic of the biosignal sensor may be one of (a) electromyographic electrodes, (b) one or more inertial measurement units, (c) one or more accelerometers, (d) one or more barometers, (e) one or more ultrasonic sensors, (f) one or more infrared sensors, (g) one or more pressure sensors, (h) one or more electroencephalogram electrodes, (i) one or more electrooculogram sensors, (j) one or more accelerometers, or (k) one or more scleral search coils.

In additional aspects, the adaptive biosignal systems and methods described herein a biosignal sensor designation switching in which sensors and the frequency of which the sensors operate are changed based on their respective designations. In many of these aspects, an electronic switch changes the designation of the biosignal sensors (e.g., electrical or mechanical) to operate in a changed, updated, or different modality. In some aspects still, the changing of the designation of the biosignal sensor may also change how the adaptive biosignal system and/or method is configured to interface with the newly designated biosignal sensor (e.g., the changing of a measurement electrode to an emission electrode, wherein an emission electrode is configured to deliver an electric impulse to the user).

The adaptive biosignal system and method for switching the designation of a biosignal sensor may, in some aspects, be configured to allow the addition or subtraction of a biosignal sensor from the biosignal detection device. In these aspects, the addition or subtraction of the biosignal sensor from the biosignal detection device may either add or subtract from the number of available sensor designation permutations, respectively.

In addition, the present disclosure includes applying the adaptive biosignal systems and methods with, or by use of, a particular machine, e.g., a biosignal detection device comprising biosignal sensors having various modalities as described herein.

Still further, the present disclosure includes effecting a transformation or reduction of a particular article to a different state or thing, e.g., transforming the control state of a biometrics device and/or biosignal sensors via the adaptive biosignal systems and methods as described herein.

The present disclosure includes specific features other than what is well-understood, routine, conventional activity in the field, and/or otherwise adds unconventional steps that confine the disclosure to a particular useful application, e.g., adaptive biosignal systems and methods for switching one or more designations of biosignal sensors for dynamic adaptation and optimization of one or more biosignal detection devices.

Advantages will become more apparent to those of ordinary skill in the art from the following description of the preferred aspects which have been shown and described by way of illustration. As will be realized, the present aspects may be capable of other and different aspects, and their details are capable of modification in various respects. Accordingly, the drawings and description are to be regarded as illustrative in nature and not as restrictive.

BRIEF DESCRIPTION OF THE DRAWINGS

The figures described below depict various aspects of the system and methods disclosed therein. It should be understood that each Figure depicts an aspect of a particular aspect of the disclosed system and methods, and that each of the Figures is intended to accord with a possible aspect thereof. Further, whenever possible, the following description refers to the reference numerals included in the following Figures, in which features depicted in multiple Figures are designated with consistent reference numerals.

DETAILED DESCRIPTION

Figure 1:
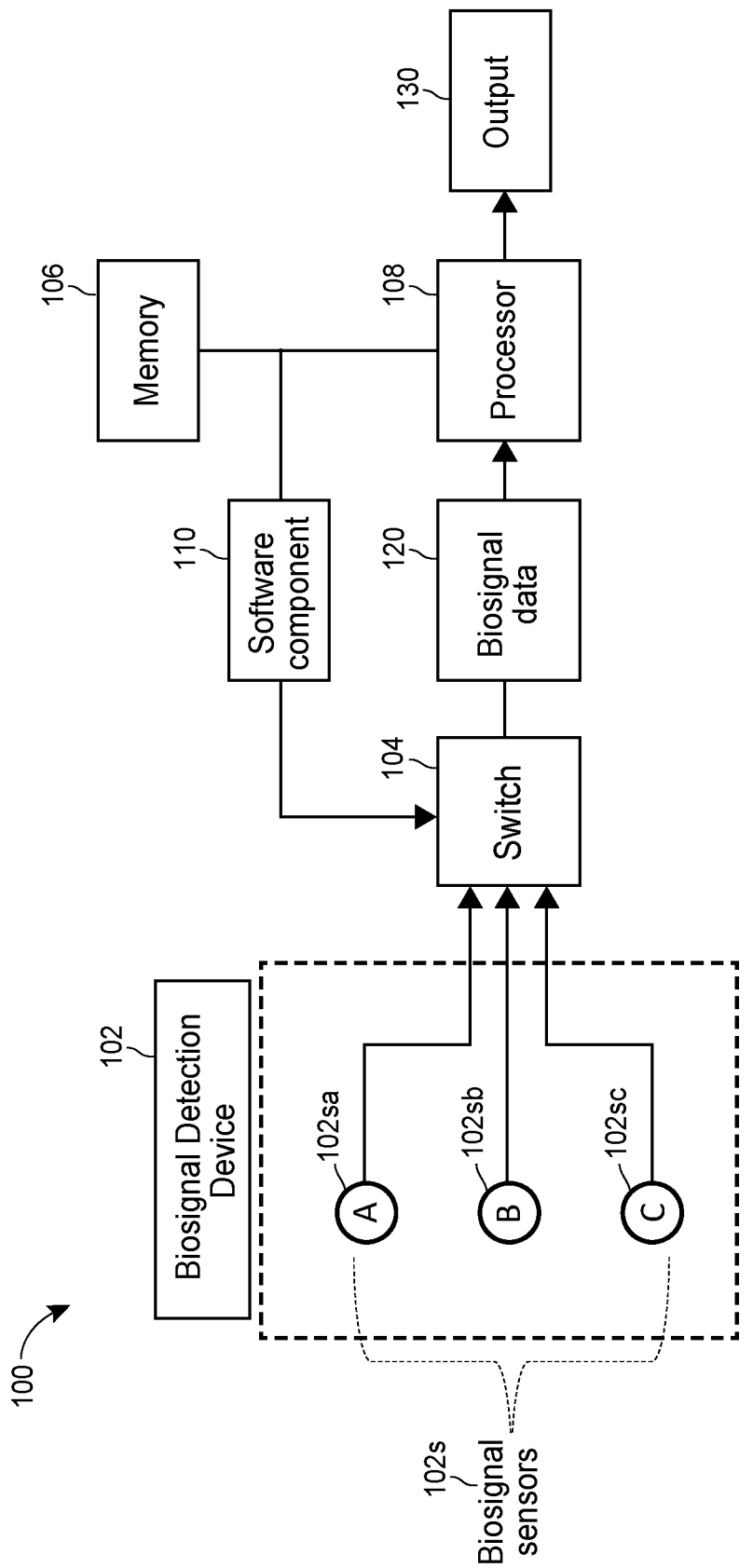
FIG. 1 is a diagram illustrating an example adaptive biosignal system configured to switch one or more designations of biosignal sensors for dynamic adaptation and optimization of a biosignal detection device, in accordance with various aspects herein.

While the present invention is susceptible of aspects in many different forms, there are shown in the drawings and will be described herein in detail specific exemplary aspects thereof, with the understanding that the present disclosure is to be considered as an exemplification of the principles of the invention and is not intended to limit the invention to the specific aspects illustrated. In this respect, before explaining at least one aspect consistent with the present invention in detail, it is to be understood that the invention is not limited in its application to the details of construction and to the arrangements of components set forth above and below, illustrated in the drawings, or as described in the examples. Methods and systems consistent with the present invention are capable of other aspects and of being practiced and carried out in various ways. Also, it is to be understood that the phraseology and terminology employed herein, as well as the abstract included below, are for the purposes of description and should not be regarded as limiting.

FIG. 1 is a diagram illustrating an example adaptive biosignal system 100 configured to switch one or more designations of biosignal sensors 102s for dynamic adaptation and optimization of a biosignal detection device 102, in accordance with various aspects herein. System 100 illustrates a non-limiting configuration illustrating interaction among a biosignal detection device 102, a switch 104, and a processor 108. It is to be understood, however, that other configurations, including different placements, or different numbers of, components of (e.g., different configurations of biosignal detection device(s) 102, switch(s) 104, and/or processor(s) 108) are contemplated herein, such that the arrangement, positioning, and/or numbers of the components of FIG. 1 is adaptable for configuration or arrangement in a given wearable or other apparatus in additional and/or different manners or configurations, for example, as described and shown for FIGS. 4A, 4B, 4C, 5, 6, and/or 7, herein.

With reference to FIG. 1, adaptive biosignal system 100 comprises a biosignal detection device 102 that includes a plurality of biosignal sensors 102s, including a first biosignal sensor 102sa, a second biosignal sensor 102sb, and a third biosignal sensor 102sc. Each of these biosignal sensors 102s may be configured to collect biosignal data 120 of a user (e.g., a user 202 as shown for FIG. 2).

In various aspects, a biosignal sensor (e.g., such as any of biosignal sensors 102s) may comprise one or more of: (a) one or more electromyographic electrodes; (b) one or more inertial measurement units; (c) one or more accelerometers; (d) one or more barometers; (e) one or more infrared sensors; (f) one or more pressure sensors; (g) one or more electroencephalogram electrodes; (h) one or more electrooculogram sensors; (i) one or more temperature sensors; and/or (j) one or more electrocardiogram sensors.

With reference to FIG. 1, adaptive biosignal system 100 further includes a switch 104 communicatively coupled to the biosignal detection device 102. In some aspects, switch 104 may receive biosignal data from biosignal sensors 102s. Additionally, or alternatively, switch 104 may send such biosignal data to processor 108 for processing and/or execution for generation of output 130.

Switch 104 may also be configured to modify a designation of one or more of the plurality of biosignal sensors 102s. Any of the biosignal sensors 102s may be adaptively configured by a designation defining an electrical sensor modality. The modality of a given biosignal sensor defines a given biosignal sensor's task, job, and/or otherwise electronic or electrical function as it operates within adaptive biosignal system 100 and/or as part of biosignal sensors 102s, for example, in relation to other biosignal sensors 102s. For example, in a various aspects, at least one of the plurality of biosignal sensors, may be configured for designation as at least one of (a) a measurement sensor (e.g., reading biosignal data of a user, including of the user's muscle contractions or the like); (b) a reference sensor (e.g., reading biosignal data of a user for baselining data as measurement by measurement sensor(s)); or, (c) a therapeutic sensor (e.g., providing an electric stimulus, heat, or other stimulus or physical output to the user, such as to the user's skin and/or muscle tissue or otherwise body portion).

For example, at least one of the plurality of biosignal sensors may be, or may be designated as, a reference sensor such that biosignal data is collected by the reference sensor as reference biosignal data. Reference biosignal may be used as base data by which other biosignal sensors may be measured. In various aspects, reference biosignal data may be used for common mode subtraction against biosignal data as collected by one or more other biosignal sensors.

In an additional non-limiting example, each of the plurality of biosignal sensors may be designated as therapeutic sensors, where each therapeutic sensor may be configured to provide of at least one of: (a) a therapeutic stimulus, and/or (b) a functional stimulus to a user (e.g., user 202).

With reference to FIG. 1, first biosignal sensor 102sa may be designated as a reference sensor, and second biosignal sensor 102sb may be designated as a measurement sensor. Switch 104 may be configured to designate one or more of the plurality of biosignal sensors 102s (e.g., any one or more of 102sa, 102sb, and/or 102sc) as at least one of (a) a measurement sensor; (b) a reference sensor; or, (c) a therapeutic sensor.

With continued reference to FIG. 1, adaptive biosignal system 100 further comprises a processor 108 communicatively coupled to biosignal detection device 102. Adaptive biosignal system 100 also includes a software component 110 comprising computing instructions stored on a memory 106 communicatively coupled to processor 108. The computing instructions, when executed by the processor, cause the processor to execute a sensor designation cycle, for example a sensor designation cycle as described for sensor designation method or algorithm 300 of FIG. 3, adaptive biosignal method 700 of FIG. 7, or elsewhere herein. The computing instructions may be implemented in one or more programming languages, such as C, C++, Java, python, or the like, where the programming instructions implement the algorithm described for FIGS. 3 and/or 7, or as otherwise described herein.

In various aspects, the instructions of the software component controls the operation of switch 104, designation of one or more of biosignal sensors 102s, and, as a result, the output 130, which may comprise output of data supplied to connected devices. For example, in various aspects, computing instructions of the software component can cause the processor 108 to: configure switch 104 to determine a designation criteria or modality for one or more of the plurality of biosignal sensors (e.g., biosignal sensors 102sa, 102sb, and/or 102sc), causing a change in output 130. Output 130 may be output to an electronic device, such as a biometric device, prosthetic device, orthopedic device, or the like, to control operation of the device or to otherwise manipulate an external device (e.g., a third-party device or a controlled device). For example, output signal (e.g., output 130) may be used to control an external device, such as a prosthetic hand, arm, leg, or other such prosthetic and/or orthopedic device or artificial body part. Additionally, or alternatively, output 130 may also be therapeutic in nature, and may comprise thermal (e.g., heat), electrical (e.g., electrical stimulus), or other such physical or therapeutic stimulus, e.g., as applied to the skin or muscle tissue of a user.

Figure 2:
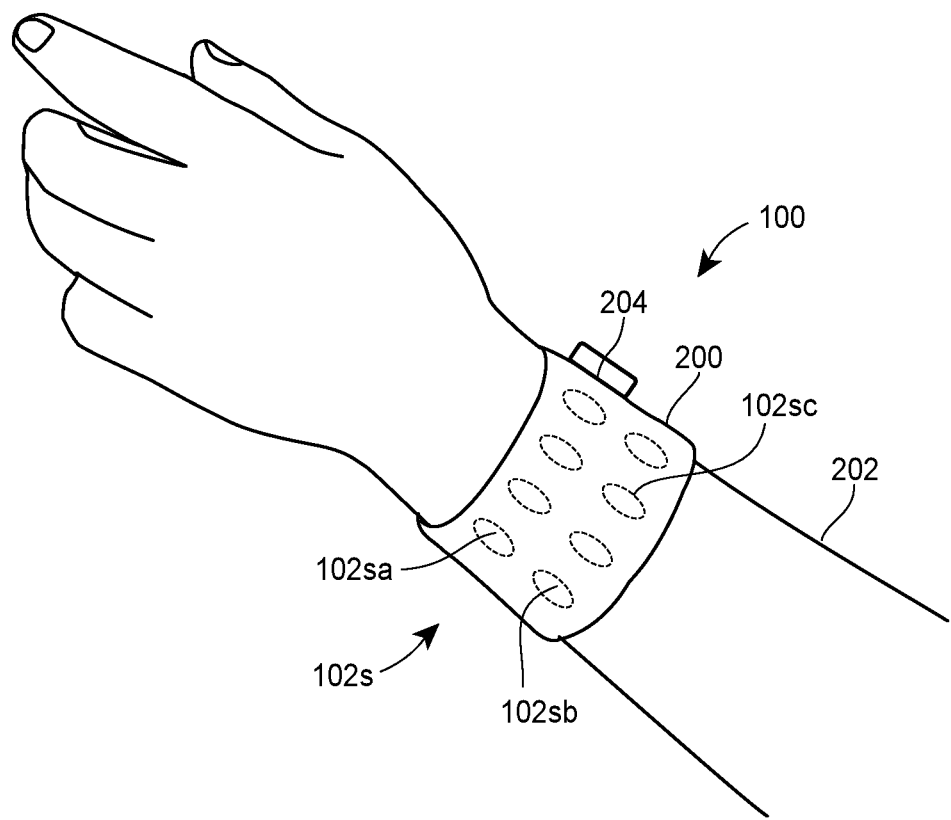
FIG. 2 is an example of the adaptive biosignal system of FIG. 1 incorporated into a wearable device, in accordance with various aspects herein.

FIG. 2 is an example of the adaptive biosignal system 100 of FIG. 1 incorporated into a wearable device 200, also known as a "wearable" (e.g., a wearable band as shown for FIG. 2). As represented by FIG. 2, an adaptive biosignal system 100 and/or biosignal detection device 102 may be incorporated within or as part of a wearable device (e.g., wearable device 200) conformable to a body portion or a shape of the user. As shown in the example of FIG. 2, a user 202 may wear the adaptive biosignal system on their arm as a device or part of a garment. It is to be understood, however, that adaptive biosignal system 100 may be incorporated into other devices, garments, or otherwise wearable or contactable apparatuses configured to attach to a user to collect biosignal data of the user.

In the example aspect of FIG. 2, user 202 is connected to biosignal system 100 comprising biosignal detection device 102 with biosignal sensors 102s, which may include biosignal sensors 102sa, 102sb, and 102sc as described for FIG. 1 herein. Configured as such, adaptive biosignal system 100 is configured to collect biosignal data of a user (e.g., user 202). In various aspects biosignal sensors 102s (e.g., including any one or more of biosignal sensors 102sa, 102sb, and 102sc). In FIG. 2, sensor 102s are depicted as electrode based sensors. However, other sensors and/or sensor combinations may be used. For example, in various aspects, sensor(s) may comprise any one or more of, e.g., EMG sensors, sonomyography (SMG) sensors, infrared (IR) sensors, inertial measurement unit (IMU) sensors, and/or as otherwise as described herein. The biometric data of the user correspond to the sensor(s) used (e.g., sensor(s) 102s) and may comprise one or more of: electromyographic (EMG) signals; electroencephalographic (EEG) signals; electrocardiographic (ECG) signals; mechanomyographic (MMG) signals; electrooculographic (EOG) signals; galvanic skin responsive (GSR) signals; magnetoencephalographic (MEG) signals; ultrasonic signals; gyroscopic signals; and/or accelerometric signals. In accordance with the above, the adaptive biosignal system 100 may comprise a biosignal detection device 102 with a unique configuration of sensors, number of sensors, and/or sensor locations, that conform to the specific anatomy of the user (e.g., user 202). Accordingly, the adaptive biosignal system 100 can adapt to each particular configuration for a given user (e.g., user 292), and be configured itself to collect and analyze the specific biometric data as collected from the user 202.

In some aspects, adaptive biosignal system 100 is configured to switch designations of biosignal sensors (e.g., biosignal sensors 102s) for dynamic adaptation and optimization of one or more biosignal detection devices (e.g., biosignal detection device 102). In such aspects, the adaptive biosignal system 100 comprises the biosignal detection device (e.g., biosignal detection device 102) comprising the plurality of biosignal sensors (e.g., biosignal sensors 102s), and where each of the plurality of biosignal sensors are configured to collect biosignal data of a user and initiate a therapeutic modality. A switch (e.g., switch 104) may be communicatively coupled to the biosignal detection device (e.g., biosignal detection device 102) and may be configured to modify a designation of one or more of the plurality of biosignal sensors (e.g., biosignal sensors 102s) where each respective designation defines an electrical sensor modality. A processor may be communicatively coupled to the biosignal detection device. And a software component comprising computing instructions stored on a memory (e.g., memory 106) may be communicatively coupled to the processor (e.g., processor 108), where the computing instructions, when executed by the processor, may cause the processor to: designate one or more of the plurality of biosignal sensors as: (a) a measurement sensor; (b) a reference sensor, or; (c) a therapeutic sensor. In aspects where the biosignal sensor comprises a therapeutic modality, such therapeutic modality may comprise at least one of: an ultrasonic modality, an electric modality, or a thermal modality. Implementation of the therapeutic modality comprises causing at least one of the biosignal sensors to create a physiological event for the user 202.

In various aspects, adaptive biosignal system 100 further comprises a processor (e.g., processor 108) communicatively coupled to biosignal sensor(s) 102s and configured to receive the biosignal data or otherwise biometric signals of the user. In some aspects, the processor (e.g., processor 108) may comprise a myoelectric prosthetic controller or processor configured or calibrated to control a prosthetic device, biometric device, or other device as may be controlled by output (e.g., output 130) or otherwise as provided from processor 108. In other aspects, the processor may be a microprocessor (e.g., embedded in a wearable device, such as wearable device 200) or other such processor configured to receive biosignal data and/or biosignal signals of a user (e.g., user 202). In some aspects, the processor (e.g., processor 108) may be included in, or be part of, or otherwise communicatively connected to, a biometric device (e.g., biosignal detection device 102).

Additionally, or alternatively, output 130 of the processor (e.g., processor 108) may be sent to, communicated to, or otherwise provided to other device(s), such as a computer or other processor-based device. In the example of FIG. 1, processor 108 may communicate via a wireless communication. For example, communication of output 130 may be via USB wired connection or via wireless transmission, e.g., via a transmitter communicating via BLUETOOTH, WIFI, or other radio-based communication standard. In some aspects, biosignal data or otherwise signal data of the user (e.g., user 202), for example as shown herein for FIG. 2, may be collected from sensor(s) 102s and transmitted or output to external devices (e.g., a prosthetic device, biometric device, etc.) for recording, visualization, analysis, training of machine learning components or models, etc. It is to be understood that output (e.g., output 130) may be provided to any electronic device, such as a mobile computing device (not shown), such as an APPLE IPHONE or ANDROID DEVICE may also be used. Such mobile device may also be connected via BLUETOOTH, etc.

As described for FIG. 1, adaptive biosignal system 100 further comprises a biometric software component comprising computing instructions executable by the processor 108. In various aspects, the adaptive biosignal system 100 comprises a tangible, non-transitory computer-readable medium (e.g., computer memory). The biometric software component may be stored on the tangible, non-transitory computer-readable medium (e.g., computer memory). The tangible, non-transitory computer-readable medium (e.g., computer memory) is configured to store instructions for dynamic adaptation and optimization of one or more biosignal detection devices (e.g., biosignal detection device 102) as described herein. For example, as described herein, execution of the computing instructions by the processor (e.g., processor 108) may cause the processor to execute a sensor designation cycle. The processor is configured to provide the control output of adaptive biosignal system 100 (e.g., output 130).

In various aspects, biosignal sensors 102s may be altered, designated, and/or re-designated. Alternation, designation, and/or re-designation of biosignal sensors 102s may cause adaptive biosignal system 100 and/or biosignal detection device 102, e.g., via processor 108, to collect different, altered, and/or reconfigured biosignal data of the user on a further, next, and/or future execution of a sensor designation cycle. That is, the alternation, designation, and/or re-designation of biosignal sensors 102s may cause adaptive biosignal system 100 and/or biosignal detection device 102 to operate differently, and/or provide different output 130, based on the different and/or altered biosignal data collected by the biosignal sensors 102s. Such alternation, designation, and/or re-designation may occur without any need for replacing, altering, adding, and/or updating physical sensors adaptive biosignal system 100 and/or biosignal detection device 102. For example, in various aspects, biosignal detection device 102 may be configured to adaptively receive or activate additional biosignal sensors. For example, in some aspects, each sensor may be physically added to biosignal detection device 102. Additionally or alternatively, each sensor may be an existing sensor already embedded in the biosignal detection device 102, where the existing sensor is activated to begin collecting biosignal data of the user. In such aspects, each addition or activation of a new biosignal sensor may increase a number of permutations of biosignal sensor groups and respective dataset groups having the new biosignal sensor (e.g., for example, the different or various configurations or permutations of biosignal sensor groups as described for FIGS. 5 and/or 6 herein). In such aspects, a new biosignal sensor, whether physically added and/or existing and activated, may be designated as at least one of: (a) a reference sensor; (b) a measurement sensor; or, (c) a therapeutic sensor.

In some aspects, alternation, designation, and/or re-designation of biosignal sensors 102s may occur via user input to an interface. For example, in some aspects, adaptive biosignal system 100 and/or biosignal detection device 102 may comprise a button 204 comprising or exposing a tactile interface. User 202 can interact with and/or receive feedback from adaptive biosignal system 100 via button 204. For example, button 204 may comprise an indicator (e.g., an LED or visual indicator; a speaker; or a haptic indicator, e.g., vibrator), where user 202 can be notified as to the alternation, designation, and/or re-designation of biosignal sensors 102s, or as to the general status, state, and/or configuration of biosignal sensors 102s, adaptive biosignal system 100, and/or biosignal detection device 102, through an auditory, tactile, or visual stimulus.

Additionally, or alternatively, adaptive biosignal system 100 may further comprise a graphic user interface (GUI) providing a virtual user interface. For example, adaptive biosignal system 100 may comprise a GUI, which may be a computer-based, virtual user interface displayed via a web page (e.g., via Active Server Pages, PHP, or the like) or desktop application. Additionally, or alternatively, the virtual user interface may comprise a mobile application-based user-interface (a mobile "app") for presentation on a mobile device (not shown), such as an APPLE IPHONE). Such visual interfaces, or GUIs, are referred to herein as "virtual user interfaces." In some aspects, biosignal data or signals of a user may be recorded in a system memory 106 (e.g., a system memory of, or as communicatively coupled to a computing or electronic device, such as biometric device 102 or otherwise of adaptive biosignal system 100). User 202 can access the biometric data or signals for viewing, review, or otherwise, e.g., via a virtual user interface, e.g., via a display of a mobile device or otherwise computer screen. In various aspects, a virtual user interface is configured to render visual feedback or otherwise views comprising one or more of: (1) the biometric signals or biosignal data of a user of the user; (2) a configuration and/or arrangement (e.g., graphical configuration and/or arrangement) of the biosignal sensors 102s (e.g., as shown in any one or more of FIGS. 4-6); and/or (3) output 130 based on the configuration and/or arrangement (e.g., graphical configuration and/or arrangement) of the biosignal sensors 102s (e.g., as shown in any one or more of FIGS. 4-6).

Figure 3:
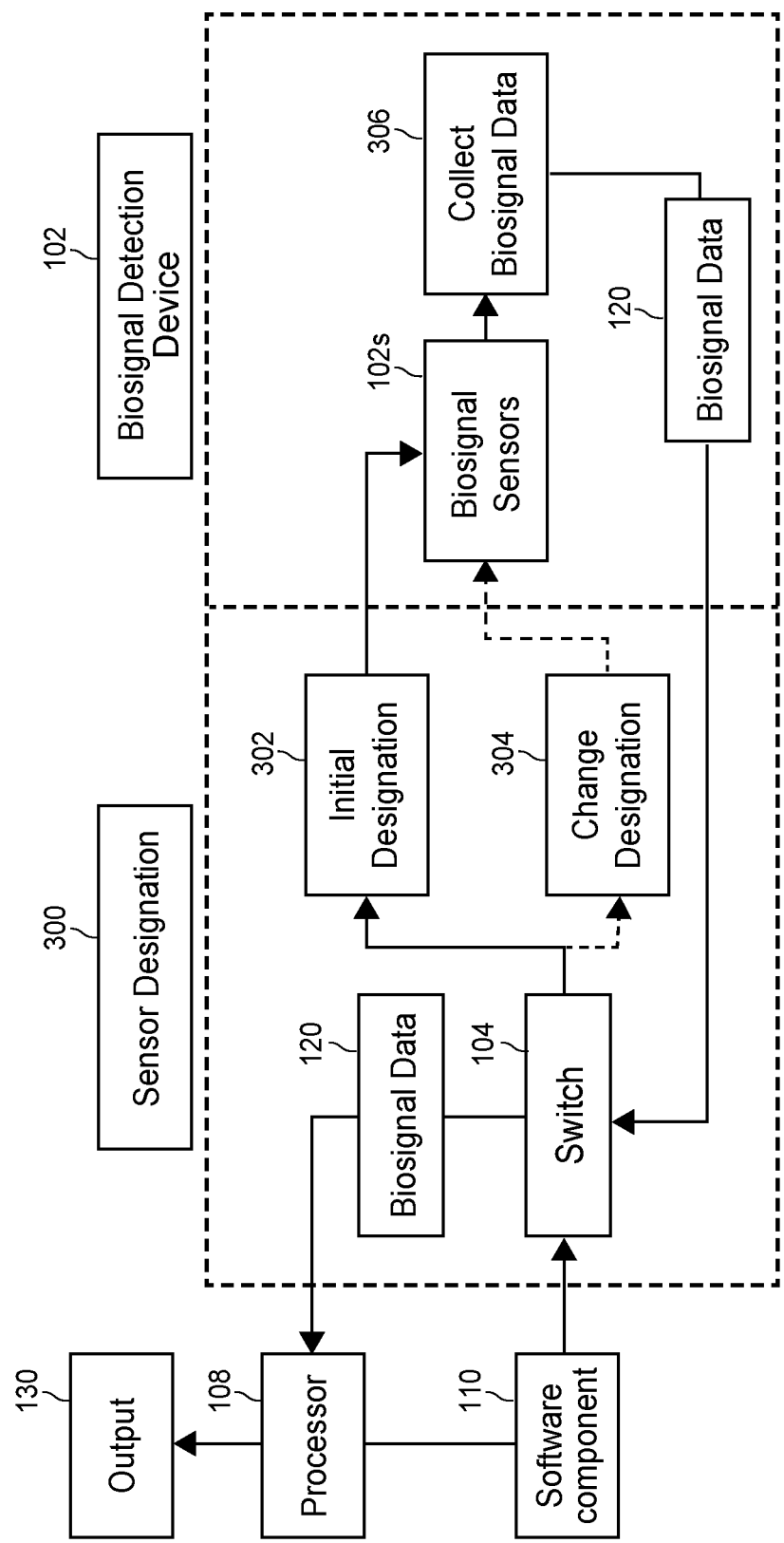
FIG. 3 is a flowchart illustrating adaptive biosignal method for switching one or more designations of biosignal sensors for dynamic adaptation and optimization of one or more biosignal detection devices, in accordance with various aspects herein.
Figure 4:
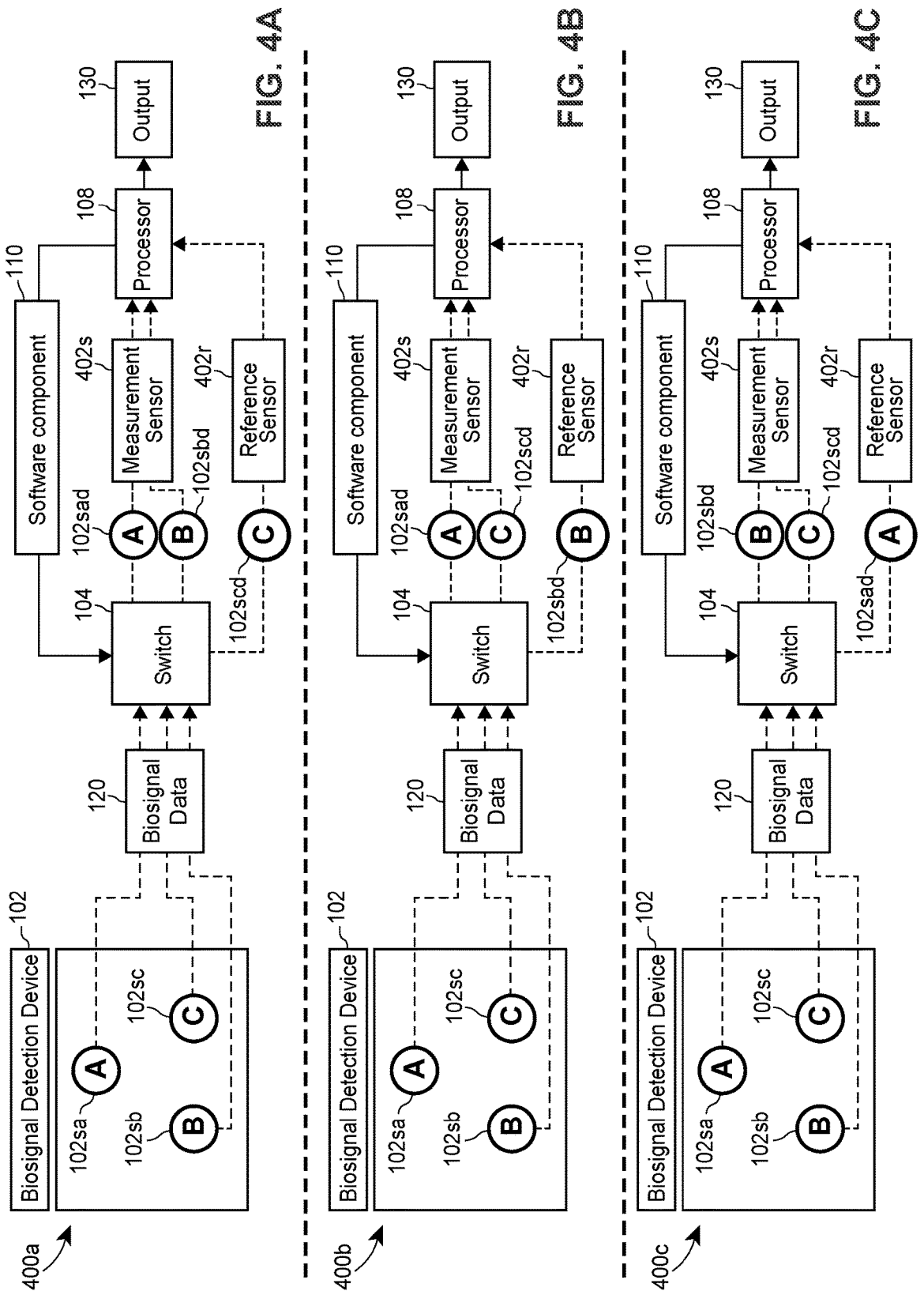
FIG. 4A is a diagram illustrating the adaptive biosignal system of FIG. 1 in a first configuration having a first permutation of biosignal sensor designations for the biosignal detection device, in accordance with various aspects herein.
FIG. 4B is a diagram illustrating the adaptive biosignal system of FIG. 1 in a second configuration having a second permutation of biosignal sensor designations for the biosignal detection device, in accordance with various aspects herein.
FIG. 4C is a diagram illustrating the adaptive biosignal system of FIG. 1 in a third configuration having a third permutation of biosignal sensor designations for the biosignal detection device, in accordance with various aspects herein.

FIG. 3 is a flowchart illustrating a sensor designation method or algorithm 300 for switching one or more designations of biosignal sensors (e.g., biosignal sensors 102s) for dynamic adaptation and optimization of one or more biosignal detection devices (e.g., biosignal detection device 102), in accordance with various aspects herein. In the example of FIG. 2, sensor designation method or algorithm 300 comprises a non-limiting switching process or algorithm for designation of one or more biosignal sensor(s) (e.g., biosignal sensors 102s) of the biosignal detection device (e.g., biosignal detection device 102) as described for FIGS. 1 and 2, in accordance with various aspects herein.

In various aspects, a software component 110 (e.g., as described for FIG. 1) comprises computing instructions stored on a memory (e.g., memory 106) communicatively coupled to a processor (e.g., processor 108). The computing instructions, when executed by the processor (e.g., processor 108), may cause the processor to execute a sensor designation cycle. The sensor designation cycle may comprise various switching routines, processes, and/or algorithm. A biological sensor (e.g., any one of biosignal sensors 102s) may have an initial designation 302, e.g., for example, an initial designation as a measurement sensor, reference sensor, or other sensor designation as described herein. In one aspect, the sensor designation cycle may comprise switching, designating, or otherwise changing, at block 304 (e.g., via control of switch 104 by software component 110 and/or processor 108), the designation of a first biosignal sensor previously designated as a reference sensor to a measurement sensor. Additionally, or alternatively, the sensor designation cycle may comprise switching, designating, or otherwise changing, at block 304 (e.g., via control of switch 104 by software component 110 and/or processor 108), the designation of a second biosignal sensor previously designated as a measurement sensor to a reference sensor. Additionally, or alternatively, the sensor designation cycle may comprise switching, designating, or otherwise changing, at block 304 (e.g., via control of switch 104 by software component 110 and/or processor 108), a third biosignal sensor as either a measurement sensor or a reference sensor.

When biosignal sensors are designated, re-designated, or otherwise changed, biosignal detection device 102 may collect biosignal data (block 306) in different, additional, new, and/or otherwise updated ways, such as collecting data from different groupings or permutations of sensors, causing output 130 correspondingly, or otherwise reflexively, to be different, additional, new, and/or otherwise updated. Additionally, or alternatively, in various aspects, the computing instructions of the software component 110 may further cause the processor (e.g., processors 108) to configure the switch (e.g., switch 104) to (a) change a sampling rate at which the biosignal data (block 306) is collected; or (b) ignore or deactivate biosignal sensors (e.g., biosignal sensors 102s) at specified intervals of the sensor designation cycle.

In some aspects, the sensor designation cycle may comprise switching, designating, or otherwise changing, at block 304 (e.g., via control of switch 104 by software component 110 and/or processor 108), one or more biosignal sensor(s) in order to form biosensor groups for the purpose of collecting biosignal data (block 306) as unique permutations or otherwise configurations of dataset groups or groupings. For example, biosignal data of a user (e.g., user 202) may be collected from at least one measurement sensor and may be analyzed in a dataset group with additional biosignal data of the user collected from at least one of (a) a reference sensor; or, (b) a second measurement sensor. In some aspects, at least one of the plurality of biosignal sensors may be configured as a reference sensor. The reference sensor may comprise or be at least one of: (a) an earth electrode; (b) a ground electrode; (c) a grounding system; (d) an earthing switch; and/or (e) an electrical earthing system.

In additional examples, the sensor designation cycle may comprise switching, designating, or otherwise changing, at block 304 (e.g., via control of switch 104 by software component 110 and/or processor 108), where a third biosignal sensor is initially designated (block 302) as a measurement sensor and where a second biosignal sensor and the third biosignal sensor initially (at block 302) comprise an initial biosignal sensor group. In such aspects, biosignal data (block 306) of the user (e.g., user 202) may be measured by the initial biosignal sensor group and may be analyzed as a first dataset group. The sensor designation cycle may comprise switching the designation of the first biosignal sensor to a measurement sensor and pairing either the first biosignal sensor with the second biosignal sensor or the third biosignal sensor to create a new biosignal sensor group. In such aspects, different biosignal data (e.g., block 306) of the user (e.g., user 202) is measured by the new biosignal sensor group as a second dataset group. The second dataset group may be different from, or otherwise updated compared to, the first dataset group.

FIGS. 4A, 4B, and 4C, illustrate different example configurations of the adaptive biosignal system 100 of FIG. 1, each having a specific permutation of biosignal sensors 102s designations and/or biosignal sensor groupings that result in unique or different dataset groups as captured by biosignal detection device 102 for user 202. By way of non-limiting example, any of the configurations as described for FIGS. 4A, 4B, and 4C may be incorporated into wearable device 200 as described for FIG. 2 herein.

FIG. 4A is a diagram illustrating the adaptive biosignal system 100 of FIG. 1 in a first configuration 400a having a first permutation of biosignal sensor designations for the biosignal detection device 102, in accordance with various aspects herein. For example, with reference to FIG. 4A, biosignal sensors 102s (e.g., including each of biosignal sensors 102sa, 102sb, and 102sc) each generate or collect biosignal data 120 of a user (e.g., user 202). Such biosignal data is fed into switch 104 that controls designations and/or otherwise data flow of the biosignal sensors 102s. In the example of FIG. 4A, each of biosignal sensors 102sa and 102sb are designated as measurement sensors (block 402s), causing data received by these sensors to be treated as, or otherwise designated or configured as, measurement data 102sad and 102sbd, respectively. In contrast, biosignal sensor 102sc is designated as a reference sensor (e.g., block 402r), causing data received by this sensor to be treated as, or otherwise designated or configured as, reference data. Processor 108 receives the measurement data and reference data as provided by each of biosignal sensors 102s and provides output 130 based on such data. Software component 110, executing on processor 108, can switch the designations by manipulating switch 104 to designate, manipulate, or otherwise configure biosignal sensors 102s, e.g., for one or more sensor designation cycle(s). For example, sensor configuration or manipulation may be configured into a different configuration as demonstrated, for example, by FIG. 4B.

FIG. 4B is a diagram illustrating the adaptive biosignal system 100 of FIG. 1 in a second configuration 400b having a second permutation of biosignal sensor designations for the biosignal detection device 102, in accordance with various aspects herein. For example, with reference to FIG. 4B, biosignal sensors 102s (e.g., including each of biosignal sensors 102sa, 102sb, and 102sc) each generate or collect biosignal data 120 of a user (e.g., user 202). Such biosignal data is fed into switch 104 that controls designations and/or otherwise data flow of the biosignal sensors 102s. In the example of FIG. 4B, each of biosignal sensors 102sa and 102sc are designated as measurement sensors (block 402s), causing data received by these sensors to be treated as, or otherwise designated or configured as, measurement data 102sad and 102scd, respectively. In contrast, biosignal sensor 102sb is designated as a reference sensor (e.g., block 402r), causing data received by this sensor to be treated as, or otherwise designated or configured as, reference data. Processor 108 receives the measurement data and reference data as provided by each of biosignal sensors 102s and provides output 130 based on such data. Software component 110, executing on processor 108, can switch the designations by manipulating switch 104 to designate, manipulate, or otherwise configure biosignal sensors 102s, e.g., for one or more sensor designation cycle(s). For example, sensor configuration or manipulation may be configured into a different configuration as demonstrated, for example, by FIG. 4C.

FIG. 4C is a diagram illustrating the adaptive biosignal system 100 of FIG. 1 in a third configuration 400c having a third permutation of biosignal sensor designations for the biosignal detection device 102, in accordance with various aspects herein. For example, with reference to FIG. 4C, biosignal sensors 102s (e.g., including each of biosignal sensors 102sa, 102sb, and 102sc) each generate or collect biosignal data 120 of a user (e.g., user 202). Such biosignal data is fed into switch 104 that controls designations and/or otherwise data flow of the biosignal sensors 102s. In the example of FIG. 4C, each of biosignal sensors 102sb and 102*sc* are designated as measurement sensors (block 402*s*), causing data received by these sensors to be treated as, or otherwise designated or configured as, measurement data 102*sbd* and 102*scd*, respectively. In contrast, biosignal sensor 102*sa* is designated as a reference sensor (e.g., block 402*r*), causing data received by this sensor to be treated as, or otherwise designated or configured as, reference data. Processor 108 receives the measurement data and reference data as provided by each of biosignal sensors 102*s* and provides output 130 based on such data. Software component 110, executing on processor 108, can switch the designations by manipulating switch 104 to designate, manipulate, or otherwise configure biosignal sensors 102*s*, e.g., for one or more sensor designation cycle(s). For example, sensor configuration or manipulation may be configured into a different configuration as demonstrated, for example, by FIGS. 4A and/or 4B, as previously described.

Figure 5:
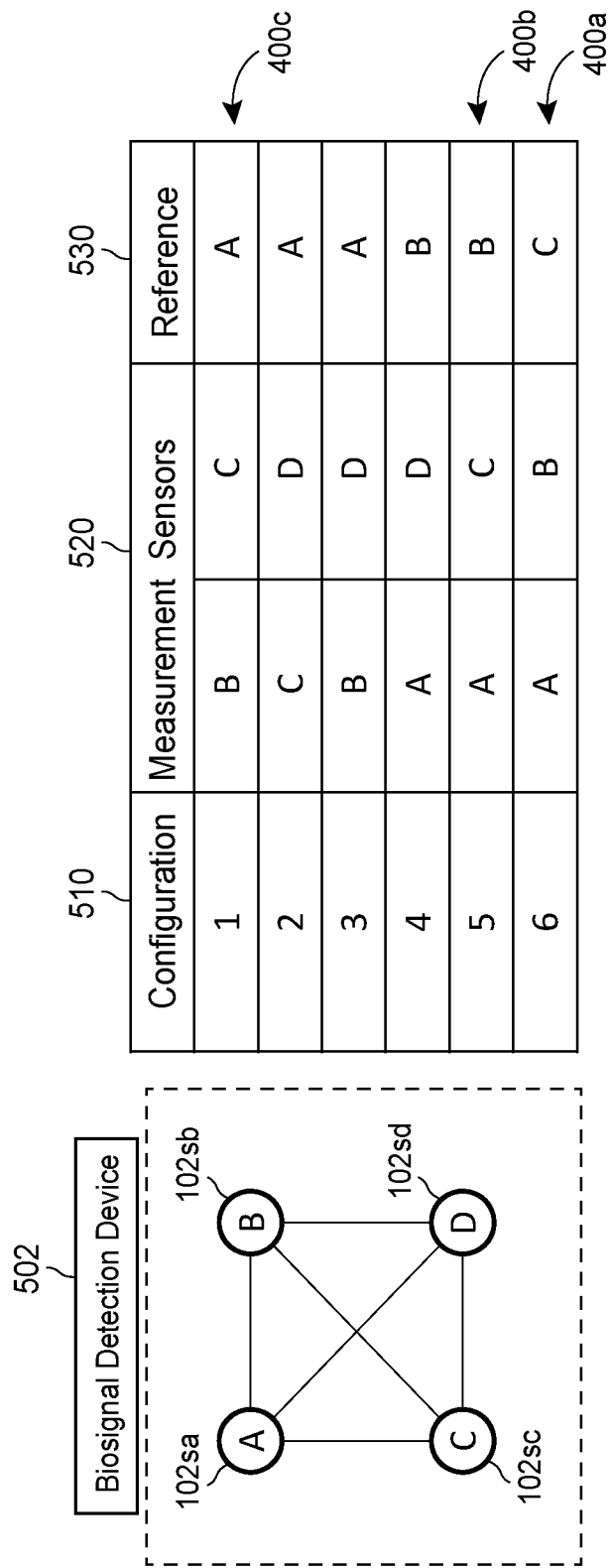
FIG. 5 is a diagram that provides an example of a biosignal detection device having four biosignal sensors and that is configurable with multiple non-redundant biosignal sensor designations forming corresponding biosignal sensor groups and related dataset groups, in accordance with various aspects herein.

FIG. 5 is a diagram that provides an example of a biosignal detection device 502 having four biosignal sensors (i.e., biosignal sensors 102*sa*, 102*b*, 102*c*, and/or 102*sd*) and that is adaptively configurable across various configurations 510 or otherwise permutations with multiple non-redundant biosignal sensor designations (e.g., measurement sensor and reference sensor designations) forming corresponding biosignal sensor groups and related dataset groups, in accordance with various aspects herein. It is to be understood that biosignal detection device 502 corresponds to biosignal detection device 102, as described, for example, with respect to FIGS. 1, 2, 3, 4A, 4B, and/or 4C, where the disclosure herein for biosignal detection device 102 applies the same or similarly herein for biosignal detection device 502. Likewise, it is to be understood that the disclosure for biosignal detection device 502 corresponds to biosignal detection device 102, such that biosignal detection device 502 may be incorporated into the systems and methods (e.g., adaptive biosignal system 100 and/or methods 300 and/or 700) as described herein for FIGS. 1, 2, 3, 4A, 4B, and/or 4C.

With reference to FIG. 5, configurations 510 (e.g., configurations 1-6) illustrate six different configurations for the sensors 102*sa*, 102*sb*, 102*sc*, and 102*sd* of biosignal detection device 502. Each configuration or otherwise permutation of configurations 510 represents a non-redundant configuration of biosignal sensors 102*sa*, 102*sb*, 102*sc*, and 102*sd*, where each of the sensors may be designated as a measurement sensor, a reference, therapeutic sensor, non-designated sensor, or other sensor as described herein. For example, configuration 1 of configurations 510 comprises designation of measurement sensors 520, where sensor 102*sb* and sensor 102*sc* are each designated as measurement sensors. Further, configuration 1 of configurations 510 comprises designation of a reference sensor, where sensor 102*sa* is designated as a reference sensor. Sensor 102*sd* is a non-designated sensor that may either be in an off state or where its sensor data is ignored. Configuration 1 of configurations 510 corresponds to third configuration 400*c* of FIG. 4C, where adaptive biosignal system 100 has designated (e.g., as part of a sensor designation cycle) the measurement and reference sensors as shown for configuration 1 of configurations 510. In such configuration, measurement data may captured and/or recorded from the measurement sensors and reference data, where measurement data is used for measuring user biosignal data and reference data is used to compare or baseline measurement data to improve the accuracy of the measuring of the user's biosignal data.

Similarly, configuration 5 of configurations 510 comprises designation of measurement sensors 520, where sensor 102*sa* and sensor 102*sc* are each designated as measurement sensors. Further, configuration 5 of configurations 510 comprises designation of a reference sensor, where sensor 102*sb* is designated as a reference sensor. Sensor 102*sd* is a non-designated sensor that may either be in an off state or where its sensor data is ignored. Configuration 5 of configurations 510 corresponds to second configuration 400*b* of FIG. 4B, where adaptive biosignal system 100 has designated (e.g., as part of a sensor designation cycle) the measurement and reference sensors as shown for configuration 5 of configurations 510. In such configuration, measurement data may captured and/or recorded from the measurement sensors and reference data, where measurement data is used for measuring user biosignal data and reference data is used to compare or baseline measurement data to improve the accuracy of the measuring of the user's biosignal data.

Still further, as another example, configuration 6 of configurations 510 comprises designation of measurement sensors 520, where sensor 102*sa* and sensor 102*sb* are each designated as measurement sensors. Further, configuration 6 of configurations 510 comprises designation of a reference sensor, where sensor 102*sc* is designated as a reference sensor. Sensor 102*sd* is a non-designated sensor that may either be in an off state or where its sensor data is ignored. Configuration 6 of configurations 510 corresponds to third configuration 400*a* of FIG. 4A, where adaptive biosignal system 100 has designated (e.g., as part of a sensor designation cycle) the measurement and reference sensors as shown for configuration 6 of configurations 510. In such configuration, measurement data may captured and/or recorded from the measurement sensors and reference data, where measurement data is used for measuring user biosignal data and reference data is used to compare or baseline measurement data to improve the accuracy of the measuring of the user's biosignal data.

Configurations 2-4 provide further examples of configurations and/or permutations of biosignal sensors 102*sa*, 102*sb*, 102*sc*, and 102*sd* of biosignal detection device 502.

Figure 6:
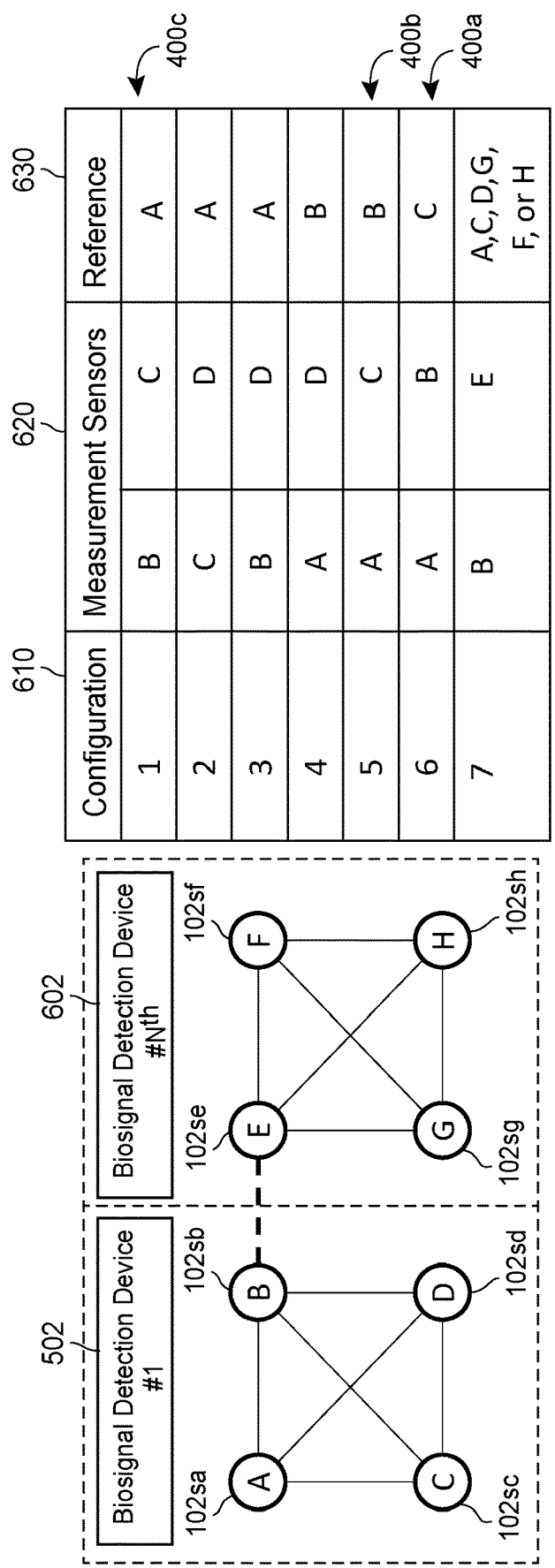
FIG. 6 demonstrates two biosignal detection devices each having four biosignal sensors, and where each biosignal detection device may utilize one another's biosignal sensor(s) as a reference for various configurations or otherwise permutations of measurement sensors across the two biosignal detection devices, in accordance with various aspects herein.

FIG. 6 demonstrates two biosignal detection devices (biosignal detection device 502 and second biosignal detection device 602), each having four biosignal sensors (e.g., biosignal sensors 102*sa*, 102*sb*, 102*sc*, 102*sd*; and biosignal sensors 102*se*, 102*sf*, 102*sg*, 102*sh*, respectively), and where each biosignal detection device may utilize one another's biosignal sensor(s) as a reference (e.g., any of reference sensors 630) for various adaptable configurations 610 or otherwise permutations of measurement sensors (e.g., any of measurement sensors 620) across the two biosignal detection devices, in accordance with various aspects herein. It is to be understood that second biosignal detection device 602, and/or the combination of biosignal detection device 502 and second biosignal detection device 602, corresponds to biosignal detection device 102, as described, for example, with respect to FIGS. 1, 2, 3, 4A, 4B, 4C, and/or 5, where the disclosure herein for biosignal detection device 102 applies the same or similarly herein for second biosignal detection device 602, and/or the combination of biosignal detection device 502 and second biosignal detection device 602. Likewise, it is to be understood that the disclosure for biosignal detection device biosignal detection device 602, and/or the combination of biosignal detection device 502 and second biosignal detection device 602, corresponds to biosignal detection device 102, such that second biosignal detection device 602, and/or the combination of biosignal detection device 502 and second biosignal detection device 602, may be incorporated into the systems and methods (e.g., adaptive biosignal system 100, and/or methods 300 or 700) as described herein for FIGS. 1, 2, 3, 4A, 4B, 4C, and/or 5.

In the aspect of FIG. 6, adaptive biosignal system 100 comprises a second biosignal detection device 602 comprising a second plurality of biosignal sensors (e.g., biosignal sensors 102se, 102sf, 102sg, 102sh) configured to collect biosignal data of the user. It is to be understood that a second biosignal detection device 602 operates in the same or similar fashion as biosignal detection device 102 as described herein. In various aspects, computing instructions of the software component 110 further cause the processor 018 to access or utilize biosignal sensors (e.g., biosignal sensors 102sa, 102sb, 102sc, 102sd; and/or biosignal sensors 102se, 102sf, 102sg, 102sh) of any designation from among any of the biosignal detection device 502 or the second biosignal detection device 602 during a sensor designation cycle.

With reference to FIG. 6, configurations 610 (e.g., configurations 1-7) illustrate seven different configurations for the biosignal sensors 102sa, 102sb, 102sc, 102sd; and/or biosignal sensors 102se, 102sf, 102sg, 102sh of biosignal detection device 502 and second biosignal detection device 602, respectively. Each configuration or otherwise permutation of configurations 610 represents a non-redundant configuration of biosignal sensors 102sa, 102sb, 102sc, 102sd; and/or biosignal sensors 102se, 102sf, 102sg, 102sh of biosignal detection device 502 and second biosignal detection device 602, respectively, where each of the sensors may be designated as a measurement sensor, a reference, or non-designated sensor. For example, configuration 1 of configurations 610 comprises designation of measurement sensors 620, where sensor 102sb and sensor 102sc are each designated as measurement sensors. Further, configuration 1 of configurations 610 comprises designation of a reference sensor, where sensor 102sa is designated as a reference sensor. Sensors 102sd, 102se, 102sf, 102sg, and/or 102sh may each be a non-designated sensor that is either off or its sensor data is ignored. Configuration 1 of configurations 610 corresponds to third configuration 400c of FIG. 4C, where adaptive biosignal system 100 has designated (e.g., as part of a sensor designation cycle) the measurement and reference sensors as shown for configuration 1 of configurations 610. In such configuration, measurement data may captured and/or recorded from the measurement sensors and reference data, where measurement data is used for measuring user biosignal data and reference data is used to compare or baseline measurement data to improve the accuracy of the measuring of the user's biosignal data.

Similarly, configuration 5 of configurations 610 comprises designation of measurement sensors 620, where sensor 102sa and sensor 102sc are each designated as measurement sensors. Further, configuration 5 of configurations 610 comprises designation of a reference sensor, where sensor 102sb is designated as a reference sensor. Sensors 102sd, 102se, 102sf, 102sg, and/or 102sh may each be a non-designated sensor that is either off or its sensor data is ignored. Configuration 5 of configurations 610 corresponds to second configuration 400b of FIG. 4B, where adaptive biosignal system 100 has designated (e.g., as part of a sensor designation cycle) the measurement and reference sensors as shown for configuration 5 of configurations 610. In such configuration, measurement data may captured and/or recorded from the measurement sensors and reference data, where measurement data is used for measuring user biosignal data and reference data is used to compare or baseline measurement data to improve the accuracy of the measuring of the user's biosignal data.

Still further, as another example, configuration 6 of configurations 610 comprises designation of measurement sensors 620, where sensor 102sa and sensor 102sb are each designated as measurement sensors. Further, configuration 6 of configurations 610 comprises designation of a reference sensor, where sensor 102sc is designated as a reference sensor. Sensors 102sd, 102se, 102sf, 102sg, and/or 102sh may each be a non-designated sensor that is either off or its sensor data is ignored. Configuration 6 of configurations 610 corresponds to third configuration 400a of FIG. 4A, where adaptive biosignal system 100 has designated (e.g., as part of a sensor designation cycle) the measurement and reference sensors as shown for configuration 6 of configurations 610. In such configuration, measurement data may captured and/or recorded from the measurement sensors and reference data, where measurement data is used for measuring user biosignal data and reference data is used to compare or baseline measurement data to improve the accuracy of the measuring of the user's biosignal data.

As an additional example, configuration 7 of configurations 610 comprises designation of measurement sensors 620, where sensor 102sb and sensor 102se are each designated as measurement sensors. In configuration 7, a permutation of multiple sensors (e.g., biosignal sensors 102sa, 102sc, 102sd, 102sg, 102sf) are designated as a biosignal sensor group, the datasets of which together form a reference dataset. More specifically, configuration 7 of configurations 610 comprises designation of a plurality of reference sensors, where biosignal sensors 102sa, 102sc, 102sd, 102sg, 102sf, and 102sh form a biosignal sensor group designated as a reference sensor group for generating a corresponding biosignal dataset group. In configuration 7, there are no sensors that are non-designated sensors that are either off or that have sensor data ignored. In such configuration, measurement data may captured and/or recorded from the measurement sensors and reference data, where measurement data is used for measuring user biosignal data and reference data is used to compare or baseline measurement data to improve the accuracy of the measuring of the user's biosignal data.

Configurations 2-4 provide further examples of configurations and/or permutations of the biosignal sensors 102sa, 102sb, 102sc, 102sd, and/or biosignal sensors 102se, 102sf, 102sg, 102sh of biosignal detection device 502 and second biosignal detection device 602, respectively.

Figure 7:
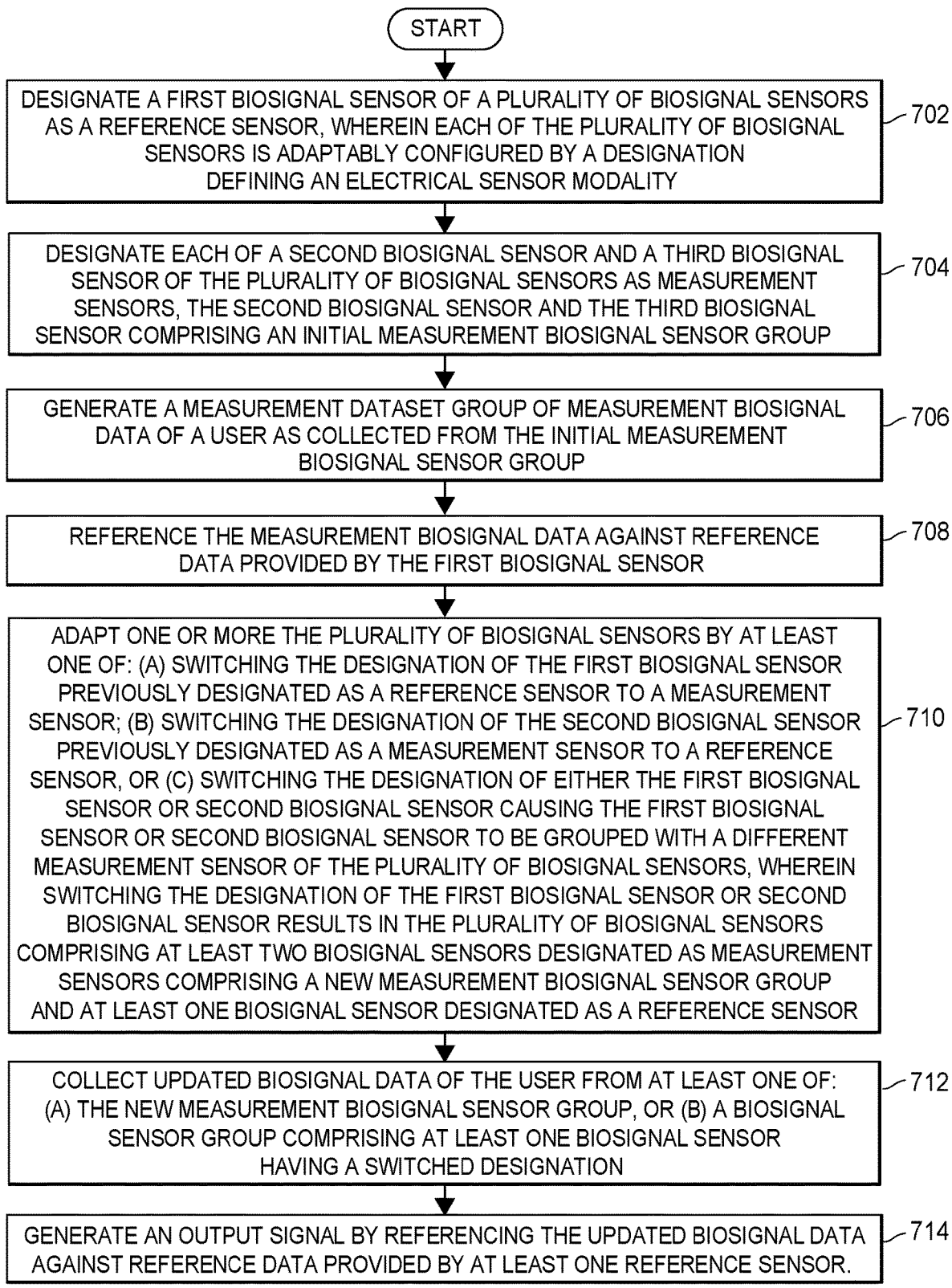
FIG. 7 illustrates a flow diagram of an adaptive biosignal method for switching biosignal sensor designations of biosignal sensors of a biosignal detection device to generate varying permutations of dataset groups comprising reference data and measurement sensor data as collected by the biosignal sensors across one or more sensor designation cycles, in accordance with various embodiments herein.

FIG. 7 illustrates a flowchart of an adaptive biosignal method 700 for switching biosignal sensor designations of biosignal sensors of a biosignal detection device to generate varying permutations of dataset groups comprising reference data and measurement sensor data as collected by the biosignal sensors across one or more sensor designation cycles. The configurations 510 and/or 610, as shown for FIGS. 5 and/or 6, may be changed, or in the alternative, maintained, over one or more sensor designation cycle(s), for example, as described for FIG. 7, or more generally, as otherwise herein, e.g., via adaptive biosignal method 300 as described herein.

With reference to FIG. 7, the adaptive biosignal method 700 comprises, at block 702, designating a first biosignal sensor (e.g., biosignal sensor 102sc) of a plurality of biosignal sensors (e.g., biosignal sensors 102sa, 102sb, 102sc, 102sd, 02se, 102sf, 102sg, 102sh) as a reference sensor (e.g., as described for any of FIGS. 1-6). It is to be understood that one or more than one biosignal sensor may be used as reference sensor(s), e.g., as described for configuration 7 of FIG. 6. Each of the plurality of biosignal sensors is adaptably configured by a designation defining an electrical sensor modality (e.g., reference; measurement, therapeutic, or otherwise as described herein).

The adaptive biosignal method 700 further comprises, at block 704, designating each of a second biosignal sensor (e.g., biosignal sensor 102sa) and a third biosignal sensor (e.g., biosignal sensor 102sb) of the plurality of biosignal sensors as measurement sensors. The second biosignal sensor and the third biosignal sensor may comprising an initial measurement biosignal sensor group (e.g., an initial designation as described for block 302 of FIG. 3 herein).

The adaptive biosignal method 700 further comprises, at block 706, generating a measurement dataset group (e.g., regarding measurement sensors 520 and/or 620 of FIGS. 5 and 6, respectively) of measurement biosignal data of a user (e.g., user 202) as collected from the initial measurement biosignal sensor group (e.g., as described for any of FIGS. 1-6).

The adaptive biosignal method 700 further comprises, at block 708, referencing the measurement biosignal data against reference data provided by the first biosignal sensor (e.g., biosignal sensor 102sc).

The adaptive biosignal method 700 further comprises, at block 710, adapting one or more the plurality of biosignal sensors (e.g., biosignal sensors 102sa, 102sb, 102sc, 102sd, 02se, 102sf, 102sg, and/or 102sh) by at least one of: (a) switching the designation of the first biosignal sensor (e.g., biosignal sensor 102sc) previously designated as a reference sensor to a measurement sensor; (b) switching the designation of the second biosignal sensor (e.g., biosignal sensor 102sa) previously designated as a measurement sensor to a reference sensor, or; (c) switching the designation of either the first biosignal sensor (e.g., biosignal sensor 102sc) or second biosignal sensor (e.g., biosignal sensor 102sa) causing the first biosignal sensor (e.g., biosignal sensor 102sc) or second biosignal sensor (e.g., biosignal sensor 102sa) to be grouped with a different measurement sensor (e.g., biosignal sensor 102se) of the plurality of biosignal sensors. Switching, e.g., by switch 104 and/or processor 108, the designation of the first biosignal sensor (e.g., biosignal sensor 102sc) or second biosignal sensor (e.g., biosignal sensor 102sa) resulting in the plurality of biosignal sensors comprising at least two biosignal sensors designated as measurement sensors (e.g., biosignal sensor 102sc and biosignal sensor 102se) comprising a new measurement biosignal sensor group and at least one biosignal sensor designated as a reference sensor (e.g., biosignal sensor 102sa).

The adaptive biosignal method 700 further comprises, at block 712, collecting updated biosignal data of the user (e.g., user 202) from at least one of: (a) the new measurement biosignal sensor group (e.g., biosignal sensor 102sc and biosignal sensor 102se), or; (b) a biosignal sensor group comprising at least one biosignal sensor having a switched designation (e.g., a biosignal sensor group comprising at least biosignal sensor 102sc having a switched designation from a reference sensor to a measurement sensor).

The adaptive biosignal method 700 further comprises, at block 714, generating an output signal (e.g., output 130) by referencing the updated biosignal data against reference data provided by at least one reference sensor (e.g., biosignal sensor 102sa, as recently designated from a measurement sensor to a reference sensor). The output signal may be used to control an external device, such as a prosthetic hand, arm, leg, or other such prosthetic and/or orthopedic device or artificial body part.

Aspects of the Present Disclosure

The following aspects of the disclosure are exemplary only and not intended to limit the scope of the disclosure.

1. An adaptive biosignal system configured to switch one or more designations of biosignal sensors for dynamic adaptation and optimization of one or more biosignal detection devices, the adaptive biosignal system comprising: a biosignal detection device comprising a plurality of biosignal sensors, each of the plurality of biosignal sensors configured to collect biosignal data of a user, and the plurality of biosignal sensors comprising at least a first biosignal sensor, a second biosignal sensor, and a third biosignal sensor; a switch communicatively coupled to the biosignal detection device and configured to modify a designation of one or more of the plurality of biosignal sensors where each respective designation defines an electrical sensor modality, wherein the first biosignal sensor is designated as a reference sensor, and wherein the second biosignal sensor is designated as a measurement sensor, a processor communicatively coupled to the biosignal detection device; and a software component comprising computing instructions stored on a memory communicatively coupled to the processor, wherein the computing instructions, when executed by the processor, cause the processor to execute a sensor designation cycle comprising of at least one of: (a) switching the designation of the first biosignal sensor previously designated as a reference sensor to a measurement sensor; (b) switching the designation of the second biosignal sensor previously designated as a measurement sensor to a reference sensor; (c) designating the third biosignal sensor as either a measurement sensor or a reference sensor; or, (d) wherein the third biosignal sensor is designated as a measurement sensor, wherein the second biosignal sensor and the third biosignal sensor comprise an initial biosignal sensor group, and wherein biosignal data of the user measured by the initial biosignal sensor group is analyzed as a first dataset group, and switching the designation of the first biosignal sensor to a measurement sensor, and pairing either the first biosignal sensor with the second biosignal sensor or the third biosignal sensor to create a new biosignal sensor group, and wherein different biosignal data of the user is measured by the new biosignal sensor group as a second dataset group, the second dataset group being different from the first dataset group.

2. The adaptive biosignal system of aspect 1, wherein at least one of the plurality of biosignal sensors is configured for designation as at least one of (a) a measurement sensor; (b) a reference sensor; or, (c) a therapeutic sensor.

3. The adaptive biosignal system as in any one of aspects 1-2, wherein biosignal data of the user collected from at least one measurement sensor is analyzed in a dataset group with biosignal data of the user collected from at least one of (a) a reference sensor; or, (b) a second measurement sensor.

4. The adaptive biosignal system as in any one of aspects 1-3, wherein the computing instructions of the software component further cause the processor to: configure the switch to change a sampling rate at which the biosignal data is collected; or, ignore or deactivate biosignal sensors at specified intervals of the sensor designation cycle.

5. The adaptive biosignal system as in any one of aspects 1-4, further comprising a second biosignal detection device comprising a second plurality of biosignal sensors configured to collect biosignal data of the user, wherein the computing instructions of the software component further cause the processor to: access or utilize biosignal sensors of any designation from among any of the biosignal detection device or the second biosignal detection device during the sensor designation cycle.

6. The adaptive biosignal system as in any one of aspects 1-5, wherein the biosignal detection device is incorporated within or as part of a wearable device conformable to a body portion or a shape of the user.

7. The adaptive biosignal system as in any one of aspects 1-6, wherein the biosignal detection device is configured to adaptively receive or activate additional biosignal sensors, each addition or activation of a new biosignal sensor increasing a number of permutations of biosignal sensor groups and respective dataset groups having the new biosignal sensor, and wherein the new biosignal sensor is designated as at least one of: (a) a reference sensor; (b) a measurement sensor; or, (c) a therapeutic sensor.

8. The adaptive biosignal system of aspect 2, wherein the at least one of the plurality of biosignal sensors is a reference sensor, and wherein the biosignal data is collected by the reference sensor as reference biosignal data, and wherein the reference biosignal data is used for common mode subtraction against biosignal data as collected by one or more other biosignal sensors.

9. The adaptive biosignal system of aspect 3, wherein the at least one of the plurality of biosignal sensors is a reference sensor, and the reference sensor includes at least one of: (a) an earth electrode; (b) a ground electrode; (c) a grounding system; (d) an earthing switch; or (e) an electrical earthing system.

10 The adaptive biosignal system as in any one of aspects 1-9, wherein the switch is configured to designate one or more of the plurality of biosignal sensors as at least one of (a) a measurement sensor; (b) a reference sensor; or, (c) a therapeutic sensor.

11. The adaptive biosignal system aspect 1, wherein the plurality of the biosignal sensors comprise one or more of: (a) one or more electromyographic electrodes; (b) one or more inertial measurement units; (c) one or more accelerometers; (d) one or more barometers; (e) one or more infrared sensors; (f) one or more pressure sensors; (g) one or more electroencephalogram electrodes; (h) one or more electrooculogram sensors; (i) one or more temperature sensors; or (j) one or more electrocardiogram sensors.

12. The adaptive biosignal system as in any one of aspects 1-11, wherein the computing instructions of the software component further cause the processor to: configure the switch to determine a designation criteria for one or more of the plurality of biosignal sensors.

13. The adaptive biosignal system of aspect 2, wherein each of the plurality of biosignal sensors are configured to be designated as therapeutic sensors, wherein each therapeutic sensor is configured to provide of at least one of: (a) a therapeutic stimulus; or (b) a functional stimulus.

14. An adaptive biosignal method for switching one or more designations of biosignal sensors for dynamic adaptation and optimization of one or more biosignal detection devices, the adaptive biosignal method comprising: executing a sensor designation cycle for a plurality of biosignal sensors of a biosignal detection device, each of the plurality of biosignal sensors configured to collect biosignal data of a user, and each of the plurality of biosignal sensors having a designation defining an electrical sensor modality modifiable by a switch communicatively coupled to the biosignal detection device, wherein the plurality of biosignal sensors comprises at least a first biosignal sensor, a second biosignal sensor, and a third biosignal sensor, wherein the first biosignal sensor is designated as a reference sensor, and wherein the second biosignal sensor is designated as a measurement sensor, the sensor designation cycle comprising of at least one of: (a) switching the designation of the first biosignal sensor previously designated as a reference sensor to a measurement sensor; (b) switching the designation of the second biosignal sensor previously designated as a measurement sensor to a reference sensor; (c) designating the third biosignal sensor as either a measurement sensor or a reference sensor; or; (d) wherein the third biosignal sensor is designated as a measurement sensor, wherein the second biosignal sensor and the third biosignal sensor comprise an initial biosignal sensor group, and wherein biosignal data of the user measured by the initial biosignal sensor group is analyzed as a first dataset group, and switching the designation of the first biosignal sensor to a measurement sensor, and pairing either the first biosignal sensor with the second biosignal sensor or the third biosignal sensor to create a new biosignal sensor group, and wherein different biosignal data of the user is measured by the new biosignal sensor group as a second dataset group, the second dataset group being different from the first dataset group.

15. The adaptive biosignal method of aspect 14, wherein at least one of the plurality of biosignal sensors is configured for designation as at least one of (a) a measurement sensor; (b) a reference sensor; or, (c) a therapeutic sensor.

16. The adaptive biosignal method as in any one of aspects 14-15, wherein biosignal data of the user collected from at least one measurement sensor is analyzed in a dataset group with biosignal data of the user collected from at least one of (a) a reference sensor; or, (b) a second measurement sensor.

17. The adaptive biosignal method as in any one of aspects 14-16, wherein the computing instructions of the software component further cause the processor to: configure the switch to change a sampling rate at which the biosignal data is collected; or, ignore or deactivate biosignal sensors at specified intervals of the sensor designation cycle.

18. The adaptive biosignal method of aspect 14-17, further comprising accessing or utilizing biosignal sensors of any designation from among any of the biosignal detection device or a second biosignal detection device during the sensor designation cycle, wherein the second biosignal detection device comprises a second plurality of biosignal sensors configured to collect biosignal data of the user.

19. A tangible, non-transitory computer-readable medium storing instructions for switching one or more designations of biosignal sensors for dynamic adaptation and optimization of one or more biosignal detection devices, that when executed by one or more processors, cause the one or more processors to: execute a sensor designation cycle for a plurality of biosignal sensors of a biosignal detection device, each of the plurality of biosignal sensors configured to collect biosignal data of a user, and each of the plurality of biosignal sensors having a designation defining an electrical sensor modality modifiable by a switch communicatively coupled to the biosignal detection device, wherein the plurality of biosignal sensors comprises at least a first biosignal sensor, a second biosignal sensor, and a third biosignal sensor, wherein the first biosignal sensor is designated as a reference sensor, and wherein the second biosignal sensor is designated as a measurement sensor, the sensor designation cycle comprising of at least one of: (a) switching the designation of the first biosignal sensor previously designated as a reference sensor to a measurement sensor; (b) switching the designation of the second biosignal sensor previously designated as a measurement sensor to a reference sensor; (c) designating the third biosignal sensor as either a measurement sensor or a reference sensor; or; (d) wherein the third biosignal sensor is designated as a measurement sensor, wherein the second biosignal sensor and the third biosignal sensor comprise an initial biosignal sensor group, and wherein biosignal data of the user measured by the initial biosignal sensor group is analyzed as a first dataset group, and switching the designation of the first biosignal sensor to a measurement sensor, and pairing either the first biosignal sensor with the second biosignal sensor or the third biosignal sensor to create a new biosignal sensor group, and wherein different biosignal data of the user is measured by the new biosignal sensor group as a second dataset group, the second dataset group being different from the first dataset group.

20. An adaptive biosignal method for switching biosignal sensor designations of biosignal sensors of a biosignal detection device to generate varying permutations of dataset groups comprising reference data and measurement sensor data as collected by the biosignal sensors across one or more sensor designation cycles, the adaptive biosignal method comprising: designating a first biosignal sensor of a plurality of biosignal sensors as a reference sensor, wherein each of the plurality of biosignal sensors is adaptably configured by a designation defining an electrical sensor modality; designating each of a second biosignal sensor and a third biosignal sensor of the plurality of biosignal sensors as measurement sensors, the second biosignal sensor and the third biosignal sensor comprising an initial measurement biosignal sensor group; generating a measurement dataset group of measurement biosignal data of a user as collected from the initial measurement biosignal sensor group; referencing the measurement biosignal data against reference data provided by the first biosignal sensor; adapting one or more the plurality of biosignal sensors by at least one of: (a) switching the designation of the first biosignal sensor previously designated as a reference sensor to a measurement sensor; (b) switching the designation of the second biosignal sensor previously designated as a measurement sensor to a reference sensor, or; (c) switching the designation of either the first biosignal sensor or second biosignal sensor causing the first biosignal sensor or second biosignal sensor to be grouped with a different measurement sensor of the plurality of biosignal sensors, wherein switching the designation of the first biosignal sensor or second biosignal sensor results in the plurality of biosignal sensors comprising at least two biosignal sensors designated as measurement sensors comprising a new measurement biosignal sensor group and at least one biosignal sensor designated as a reference sensor; collecting updated biosignal data of the user from at least one of: (a) the new measurement biosignal sensor group, or; (b) a biosignal sensor group comprising at least one biosignal sensor having a switched designation; and generating an output signal by referencing the updated biosignal data against reference data provided by at least one reference sensor.

21. An adaptive biosignal system configured to switch designations of biosignal sensors for dynamic adaptation and optimization of one or more biosignal detection devices, the adaptive biosignal system comprising: a biosignal detection device comprising a plurality of biosignal sensors, each of the plurality of biosignal sensors configured to collect biosignal data of a user and initiate a therapeutic modality; a switch communicatively coupled to the biosignal detection device and configured to modify a designation of one or more of the plurality of biosignal sensors where each respective designation defines an electrical sensor modality; a processor communicatively coupled to the biosignal detection device; and a software component comprising computing instructions stored on a memory communicatively coupled to the processor, wherein the computing instructions, when executed by the processor, cause the processor to: designate one or more of the plurality of biosignal sensors as: (a) a measurement sensor; (b) a reference sensor, or; (c) a therapeutic sensor.

22. The adaptive biosignal system of aspect 21, wherein the therapeutic modality comprises at least one of: an ultrasonic modality, an electric modality, or a thermal modality, wherein implementation of the therapeutic modality comprises causing at least one of the biosignal sensors to create a physiological event for the user.

ADDITIONAL CONSIDERATIONS

Although the disclosure herein sets forth a detailed description of numerous different aspects, it should be understood that the legal scope of the description is defined by the words of the claims set forth at the end of this patent and equivalents. The detailed description is to be construed as exemplary only and does not describe every possible aspect since describing every possible aspect would be impractical. Numerous alternative aspects may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain aspects are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example aspects, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various aspects, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering aspects in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In aspects in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example aspects, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example aspects, the processor or processors may be located in a single location, while in other aspects the processors may be distributed across a number of locations.

The performance of certain of the operations may be distributed among the one or more processors, not only residing within a single machine, but deployed across a number of machines. In some example aspects, the one or more processors or processor-implemented modules may be located in a single geographic location (e.g., within a home environment, an office environment, or a server farm). In other aspects, the one or more processors or processor-implemented modules may be distributed across a number of geographic locations.

This detailed description is to be construed as exemplary only and does not describe every possible aspect, as describing every possible aspect would be impractical, if not impossible. A person of ordinary skill in the art may implement numerous alternate aspects, using either current technology or technology developed after the filing date of this application.

Those of ordinary skill in the art will recognize that a wide variety of modifications, alterations, and combinations can be made with respect to the above described aspects without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. An adaptive biosignal system, the adaptive biosignal system comprising:
   a biosignal detection device comprising a plurality of biosignal sensors, each of the plurality of biosignal sensors configured to sense biosignal data of a user, and the plurality of biosignal sensors comprising at least a first biosignal sensor, a second biosignal sensor, and a third biosignal sensor;
   a switch communicatively coupled to the biosignal detection device and configured to modify a designation of one or more of the plurality of biosignal sensors where each of the respective designation defines an electrical sensor modality,
      wherein the first biosignal sensor is designated as a reference sensor, and wherein the second biosignal sensor is designated as a measurement sensor, a processor communicatively coupled to the biosignal detection device; and
   a software component comprising computing instructions stored on a memory communicatively coupled to the processor, wherein the computing instructions, when executed by the processor, cause the processor to execute a sensor designation cycle comprising of at least one of:
   (a) switching the designation of the first biosignal sensor previously having a reference sensor designation to a measurement sensor designation;
   (b) switching the designation of the second biosignal sensor previously having a measurement sensor designation to a reference sensor designation;
   (c) designating the third biosignal sensor as either a measurement sensor or a reference sensor; or,
   (d) wherein the third biosignal sensor is designated as a measurement sensor designation, wherein the second biosignal sensor and the third biosignal sensor comprise an initial biosignal sensor group, and wherein first biosignal data of the user measured by the initial biosignal sensor group is analyzed as a first dataset group, and switching the designation of the first biosignal sensor to a measurement sensor designation, and pairing either the first biosignal sensor with the second biosignal sensor or the third biosignal sensor to create a new biosignal sensor group, and wherein different biosignal data of the user is measured by the new biosignal sensor group as a second dataset group, the second dataset group being different from the first dataset group; and collecting the biosignal data of the first dataset group and of the second dataset group, wherein the processor is capable of executing at least sensor designation cycles (a) and (b).

2. The adaptive biosignal system of claim 1, wherein at least one of the plurality of biosignal sensors is configured for at least one of (a) a measurement sensor designation; (b) a reference sensor designation; or, (c) a therapeutic sensor designation.

3. The adaptive biosignal system of claim 2, wherein the at least one of the plurality of biosignal sensors is a reference sensor, and wherein the biosignal data is collected by the reference sensor as reference biosignal data, and wherein the reference biosignal data is used for common mode subtraction against biosignal data as collected by one or more other biosignal sensors.

4. The adaptive biosignal system of claim 2, wherein each of the plurality of biosignal sensors are configured to be designated as therapeutic stimulators, wherein each therapeutic stimulator is configured to provide of at least one of: (a) a therapeutic stimulus; or (b) a functional stimulus.

5. The adaptive biosignal system of claim 1, wherein the biosignal data of the user collected from the measurement sensor is analyzed in a dataset group with biosignal data of the user collected from at least one of (a) a reference sensor; or, (b) a second measurement sensor.

6. The adaptive biosignal system of claim 5, wherein the at least one of the plurality of biosignal sensors is a reference sensor, and the reference sensor includes at least one of: (a) an earth electrode; (b) a ground electrode; (c) a grounding system; (d) an earthing switch; or (e) an electrical earthing system.

7. The adaptive biosignal system of claim 1, wherein the computing instructions of the software component further cause the processor to:

configure the switch to change a sampling rate at which the biosignal data is collected; or, ignore or deactivate one or more of the plurality of biosignal sensors at specified intervals of the sensor designation cycle.

8. The adaptive biosignal system of claim 1, further comprising a second biosignal detection device comprising a second plurality of biosignal sensors configured to collect biosignal data of the user, wherein the computing instructions of the software component further cause the processor to:

access or utilize the plurality of biosignal sensors of the biosignal detection device or access or utilize the second plurality of biosignal sensors of the second biosignal detection device during the sensor designation cycle.

9. The adaptive biosignal system of claim 1, wherein the biosignal detection device is incorporated within or as part of a wearable device conformable to a body portion or a shape of the user.

10. The adaptive biosignal system of claim 1, wherein the biosignal detection device is configured to adaptively receive or activate additional biosignal sensors, each addition or activation of a new biosignal sensor increasing a number of permutations of biosignal sensor groups and respective dataset groups having the new biosignal sensor, and wherein the new biosignal sensor is designated as at least one of: (a) a reference sensor; (b) a measurement sensor; or, (c) a therapeutic sensor.

11. The adaptive biosignal system of claim 1, wherein the switch is configured to designate one or more of the plurality of biosignal sensors as at least one of (a) a measurement sensor; (b) a reference sensor; or, (c) a therapeutic sensor.

12. The adaptive biosignal system claim 1, wherein the plurality of the biosignal sensors comprise one or more of: (a) one or more electromyographic electrodes; (b) one or more inertial measurement units; (c) one or more accelerometers; (d) one or more barometers; (e) one or more infrared sensors; (f) one or more pressure sensors; (g) one or more electroencephalogram electrodes; (h) one or more electrooculogram sensors; (i) one or more temperature sensors; or (j) one or more electrocardiogram sensors.

13. The adaptive biosignal system of claim 1, wherein the computing instructions of the software component further cause the processor to:

configure the switch to determine a designation criteria for one or more of the plurality of biosignal sensors.

14. An adaptive biosignal method, the adaptive biosignal method comprising:

executing a sensor designation cycle for a plurality of biosignal sensors of a biosignal detection device, each of the plurality of biosignal sensors configured to collect biosignal data of a user, and each of the plurality of biosignal sensors having a designation defining an electrical sensor modality modifiable by a switch communicatively coupled to the biosignal detection device, wherein the plurality of biosignal sensors comprises at least a first biosignal sensor, a second biosignal sensor, and a third biosignal sensor, wherein the first biosignal sensor is designated as a reference sensor, and wherein the second biosignal sensor is designated as a measurement sensor, the sensor designation cycle comprising of at least one of:

(a) switching the designation of the first biosignal sensor previously having a reference sensor designation to a measurement sensor designation;

(b) switching the designation of the second biosignal sensor previously having a measurement sensor designation to a reference sensor designation;

(c) designating the third biosignal sensor as either a measurement sensor or a reference sensor; or;

(d) wherein the third biosignal sensor is designated as a measurement sensor designation, wherein the second biosignal sensor and the third biosignal sensor comprise an initial biosignal sensor group, and wherein first biosignal data of the user measured by the initial biosignal sensor group is analyzed as a first dataset group, and switching the designation of the first biosignal sensor to a measurement sensor designation, and pairing either the first biosignal sensor with the second biosignal sensor or the third biosignal sensor to create a new biosignal sensor group, and wherein different biosignal data of the user is measured by the new biosignal sensor group as a second dataset group, the second dataset group being different from the first dataset group; and collecting the biosignal data of the first dataset group and of the second dataset group, wherein the processor is capable of executing at least sensor designation cycles (a) and (b).

15. The adaptive biosignal method of claim 14, wherein at least one of the plurality of biosignal sensors is configured for at least one of (a) a measurement sensor designation; (b) a reference sensor designation; or, (c) a therapeutic sensor designation.

16. The adaptive biosignal method of claim 14, wherein the biosignal data of the user collected from the measurement sensor is analyzed in a dataset group with biosignal data of the user collected from at least one of (a) a reference sensor; or, (b) a second measurement sensor.

17. The adaptive biosignal method of claim 14, wherein the computing instructions of the software component further cause the processor to:
configure the switch to change a sampling rate at which the biosignal data is collected; or, ignore or deactivate one or more of the plurality of biosignal sensors at specified intervals of the sensor designation cycle.

18. The adaptive biosignal method of claim 14, further comprising accessing or utilizing the plurality of biosignal sensors of the biosignal detection device or accessing or utilizing a second plurality of biosignal sensors of a second biosignal detection device during the sensor designation cycle,
wherein the second biosignal detection device comprises the second plurality of biosignal sensors configured to collect biosignal data of the user.

19. A tangible, non-transitory computer-readable medium storing instructions that when executed by one or more processors, cause the one or more processors to:
execute a sensor designation cycle for a plurality of biosignal sensors of a biosignal detection device, each of the plurality of biosignal sensors configured to collect biosignal data of a user, and each of the plurality of biosignal sensors having a designation defining an electrical sensor modality modifiable by a switch communicatively coupled to the biosignal detection device,
wherein the plurality of biosignal sensors comprises at least a first biosignal sensor, a second biosignal sensor, and a third biosignal sensor,
wherein the first biosignal sensor is designated as a reference sensor, and wherein the second biosignal sensor is designated as a measurement sensor, the sensor designation cycle comprising of at least one of:
(a) switching the designation of the first biosignal sensor previously having a reference sensor designation to a measurement sensor designation;
(b) switching the designation of the second biosignal sensor previously having a measurement sensor designation to a reference sensor designation;
(c) designating the third biosignal sensor as either a measurement sensor or a reference sensor; or,
(d) wherein the third biosignal sensor is designated as a measurement sensor designation, wherein the second biosignal sensor and the third biosignal sensor comprise an initial biosignal sensor group, and wherein first biosignal data of the user measured by the initial biosignal sensor group is analyzed as a first dataset group, and switching the designation of the first biosignal sensor to a measurement sensor designation, and pairing either the first biosignal sensor with the second biosignal sensor or the third biosignal sensor to create a new biosignal sensor group, and wherein different biosignal data of the user is measured by the new biosignal sensor group as a second dataset group, the second dataset group being different from the first dataset group; and
collecting the biosignal data of the first dataset group and of the second dataset group,
wherein the processor is capable of executing at least sensor designation cycles (a) and (b).

20. An adaptive biosignal system, the adaptive biosignal system comprising:
a biosignal detection device comprising a plurality of biosignal sensors, each of the plurality of biosignal sensors configured to collect biosignal data of a user and initiate a therapeutic modality;
a switch communicatively coupled to the biosignal detection device and configured to modify a designation of one or more of the plurality of biosignal sensors where each of the respective designation defines an electrical sensor modality;
a processor communicatively coupled to the biosignal detection device; and
a software component comprising computing instructions stored on a memory communicatively coupled to the processor, wherein the computing instructions, when executed by the processor, cause the processor to:
designate the one or more of the plurality of biosignal sensors as:
(a) a measurement sensor; (b) a reference sensor, or; (c) a therapeutic sensor; and
collect the biosignal data of the user according to the therapeutic modality.

21. The adaptive biosignal system of claim 20, wherein the therapeutic modality comprises at least one of: an ultrasonic modality, an electric modality, or a thermal modality, wherein implementation of the therapeutic modality comprises causing at least one of the biosignal sensors to create a physiological event for the user.

* * * * *